US010961508B2

(12) United States Patent
Osafune et al.

(10) Patent No.: US 10,961,508 B2
(45) Date of Patent: Mar. 30, 2021

(54) METHOD FOR INDUCING ALVEOLAR EPITHELIAL PROGENITOR CELLS

(71) Applicant: Kyoto University, Kyoto (JP)

(72) Inventors: Kenji Osafune, Kyoto (JP); Shimpei Gotoh, Kyoto (JP); Isao Ito, Kyoto (JP); Michiaki Mishima, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 101 days.

(21) Appl. No.: 14/783,382

(22) PCT Filed: Apr. 14, 2014

(86) PCT No.: PCT/JP2014/061106
§ 371 (c)(1),
(2) Date: Oct. 8, 2015

(87) PCT Pub. No.: WO2014/168264
PCT Pub. Date: Oct. 16, 2014

(65) Prior Publication Data
US 2016/0068816 A1 Mar. 10, 2016

(30) Foreign Application Priority Data

Apr. 12, 2013 (JP) ............................. JP2013-084034

(51) Int. Cl.
C12N 5/071 (2010.01)
(52) U.S. Cl.
CPC ........ C12N 5/0688 (2013.01); C12N 2500/38 (2013.01); C12N 2501/01 (2013.01); C12N 2501/065 (2013.01); C12N 2501/117 (2013.01); C12N 2501/119 (2013.01); C12N 2501/15 (2013.01); C12N 2501/155 (2013.01); C12N 2501/16 (2013.01); C12N 2501/385 (2013.01); C12N 2501/39 (2013.01); C12N 2501/415 (2013.01); C12N 2501/727 (2013.01); C12N 2501/73 (2013.01); C12N 2501/999 (2013.01); C12N 2506/45 (2013.01)
(58) Field of Classification Search
CPC .......................... C12N 2506/45; C12N 5/0688
See application file for complete search history.

(56) References Cited

U.S. PATENT DOCUMENTS

| 5,843,780 A | 12/1998 | Thomson | |
|---|---|---|---|
| 2013/0122536 A1* | 5/2013 | Osafune | C12N 5/0603 435/29 |
| 2013/0224116 A1* | 8/2013 | Bonder | A61K 35/44 424/9.1 |
| 2016/0068816 A1 | 3/2016 | Osafune et al. | |

FOREIGN PATENT DOCUMENTS

| EP | 2484754 A1 | 8/2012 |
|---|---|---|
| JP | 2014023519 A | 2/2014 |
| WO | 2007/069666 A1 | 6/2007 |
| WO | 2011139628 A1 | 11/2011 |
| WO | 2014/018691 A1 | 1/2014 |
| WO | 2014052458 A1 | 4/2014 |
| WO | 2014/168264 A1 | 10/2014 |

OTHER PUBLICATIONS

Barkauskas et al. J Clin Invest. 2013;123(7):3025-3036.*
Griffin et al. "Alveolar type II cell-fibroblast interactions, synthesis and secretion of surfactant and type I collagen" Journal of Cell Science 105, 423-432 (1993).*
Dieteren et al., "Carboxypeptidase M: Multiple alliances and unknown partners", Clinica Chimica Acta, 2009, vol. 399, No. 1-2, pp. 24-39.
Supplementary European Search Report for European Application No. EP 14782957, dated Aug. 8, 2016 (4 pages).
Rippon et al., "Initial Observations on the Effect of Medium Composition on the Differentiation of Murine Embryonic Stem Cells to Alveolar Type II Cells", Cloning and Stem Cells, 2004, vol. 6, No. 2, pp. 49-56.
Coraux et al., "Embryonic Stem Cells Generate Airway Epithelial Tissue", American Journal of Respiratory Cell and Molecular Biology, 2005, vol. 32, pp. 87-92.
Morrisey et al., "Preparing for the First Breath: Genetic and Cellular Mechanisms in Lung Development", Developmental Cell, 2010, vol. 18, pp. 8-23.
Schmeckebier et al., "Keratinocyte Growth Factor and Dexamethasone Plus Elevated cAMP Levels Synergistically Support Pluripotent Stem Cell Differentiation into Alveolar Epithelial Type II Cells", Tissue Engineering, 2013, vol. 19, No. 7-8, pp. 938-951.
Longmire et al., "Efficient Derivation of Purified Lung and Thyroid Progenitors from Embryonic Stem Cells", Cell Stem Cell, 2012, vol. 10, pp. 398-411.
Green et al., "Generation of anterior foregut endoderm from human embryonic and induced pluripotent stem cells", Nature Biotechnology, 2011, vol. 29, No. 3, pp. 267-272.
Bone et al., "A novel chemically directed route for the generation of definitive endoderm from human embryonic stem cells based on inhibition of GSK-3", Journal of Cell Science, 2011, vol. 124, No. 12, pp. 1992-2000.
Mou et al., "Generation of Multipotent Lung and Airway Progenitors from Mouse ESCs and Patient-Specific Cystic Fibrosis iPSCs", Cell Stem Cell, 2012, vol. 10, pp. 385-397.
Norrman et al., "Distinct gene expression signatures in human embryonic stem cells differentiated towards definitive endoderm at single-cell level", Methods, 2012, vol. 59, pp. 59-70.
Williams, "Alveolar Type I Cells: Molecular Phenotype and Development", Annual Review of Physiology, 2003, vol. 65, pp. 669-695.
Horalkova et al., "Characterisation of the R3/1 cell line as an alveolar epithelial cell model for drug disposition studies", European Journal of Pharmaceutical Sciences, 2009, vol. 36, pp. 444-450.

(Continued)

Primary Examiner — Blaine Lankford
(74) Attorney, Agent, or Firm — Lucas & Mercanti, LLP

(57) ABSTRACT

This invention provides a method for stably producing alveolar epithelial progenitor cells from pluripotent stem cells, including steps of culturing pluripotent stem cells in (1) a medium containing activin A and a GSK3β inhibitor, (2) a medium containing a BMP inhibitor and a TGFβ inhibitor, and (3) a medium containing BMP4, retinoic acid, and a GSK3β inhibitor.

20 Claims, 17 Drawing Sheets

(56) References Cited

OTHER PUBLICATIONS

Ikeda et al., "Differential expression of carboxypeptidase M during lung development", Cell Structure and Function, 2004, vol. 29, pp. 53.

Fujiwara et al., "Monoclonal antibody 7F9 recognizes rat protein homologous to human carboxypeptidase-M in developing and adult rat lung", Respirology, 2007, vol. 12, pp. 54-62.

International Search Report dated Jul. 22, 2014, which was issued for International PCT Application No. PCT/JP2014/061106, along with English Translations, (11 pages).

Rippon, H. J. et al., Cloning Stem Cells, 6: 49-56, 2004.

Sheppard, "ROCKing pulmonary fibrosis", The Journal of Clinical Investigation, 123.3 (2013), pp. 1005-1006.

Supplementary European Search Report issued in connection with corresponding European Patent Application No. 16761771.1, dated Jul. 27, 2018.

A. L. Firth et al., "Generation of multiciliated cells in functional airway epithelia from human induced pluripotent stem cells," Proceedings of the National Academy of Sciences, Mar. 24, 2014, pp. E1723-E1730, vol. 111, No. 17.

Van der Velden et al., "LysoTracker is a marker of differentiated alveolar type II cells", Respiratory Research, 14.1 (2013), p. 123.

Foster et al., "The Rho pathway mediates transition to an alveolar type I cell phenotype during static stretch of alveolar type 11 cells", Pediatric Research, 67.6 (2010), p. 585.

Ghaedi, M. et al., J. Clin. Invest., vol. 123, pp. 4950-4962, 2013.

Gotoh, et al., "Generation of alveolar epithelial spheroids via isolated progenitor cells from human pluripotent stem cells", Stem cell reports, 3.3 (Aug. 21, 2014), pp. 394-403.

Huang, S. X. et al., Nat. Biotechnol., vol. 32, pp. 84-91, 2014.

Kalla et al., "Thyroid transcription factor in differentiating type II cells: regulation, isoforms, and target genes", American Journal of Respiratory Cell and Molecular Biology, 36.2 (2007), p. 213-225.

Mancia et al., "Cryopreservation and in vitro culture of primary cell types from lung tissue of a stranded pygmy sperm whale (*Kogia breviceps*)", Comparative Biochemistry and Physiology Part C: Toxicology & Pharmacology, 155.1 (2012), pp. 136-142.

Morrisey, E. E. and Hogan, B. L. M., Dev. Cell., 18: 8-23, 2010.

\* cited by examiner

Fig. 1
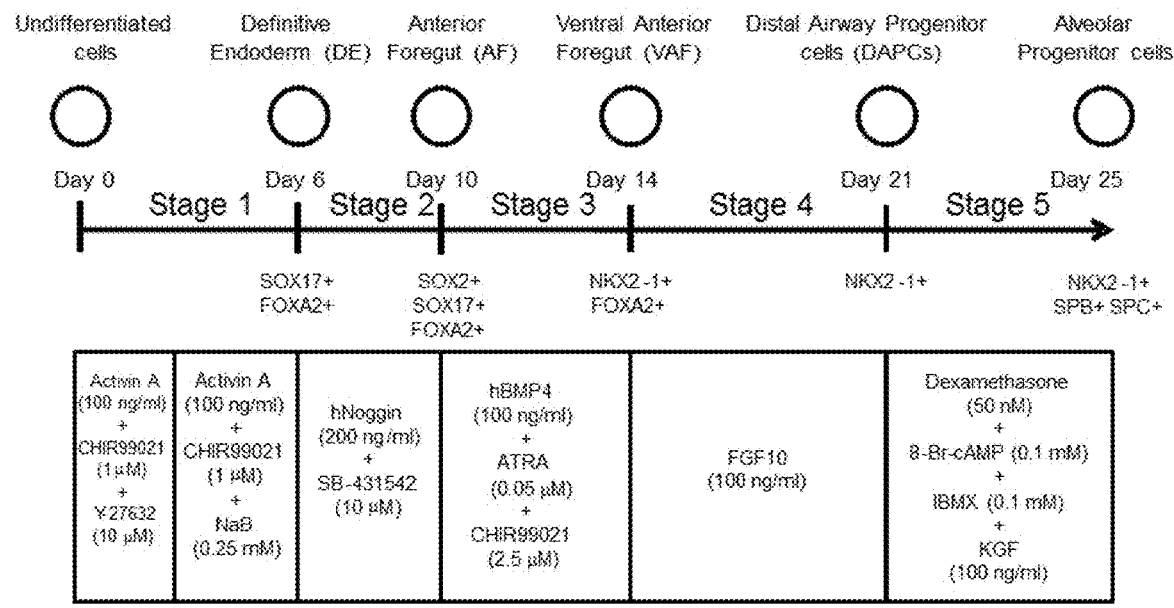
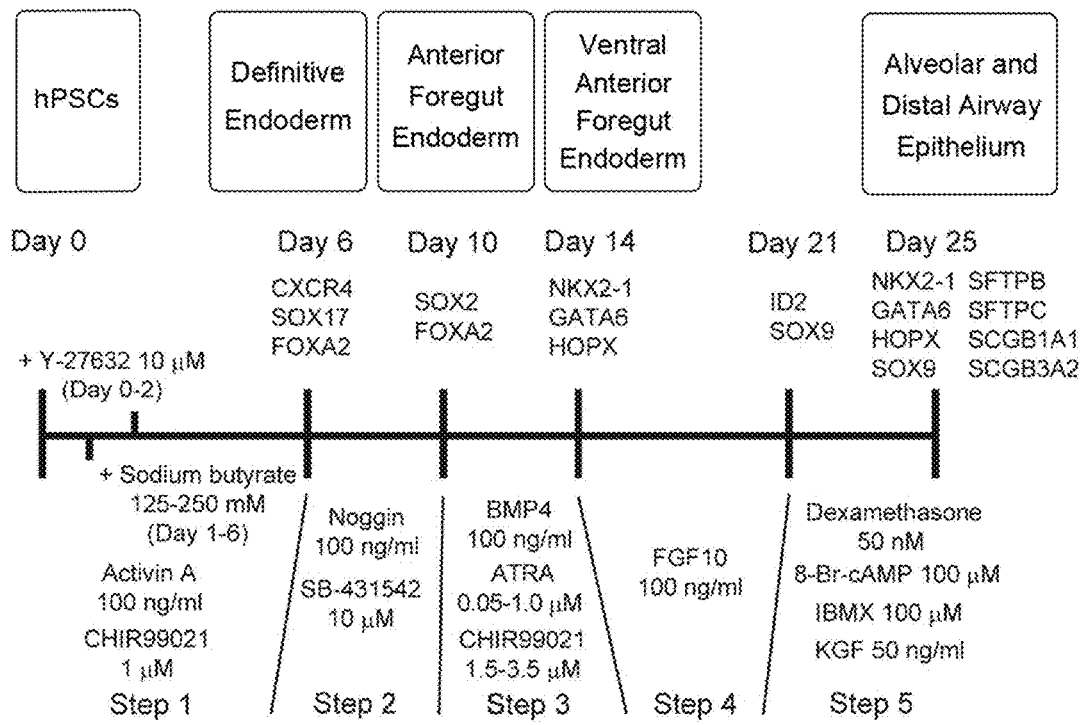

Fig. 2
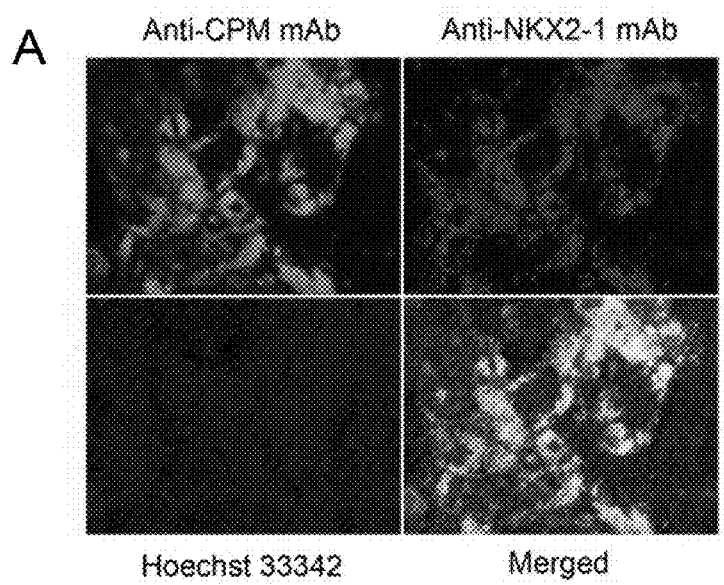
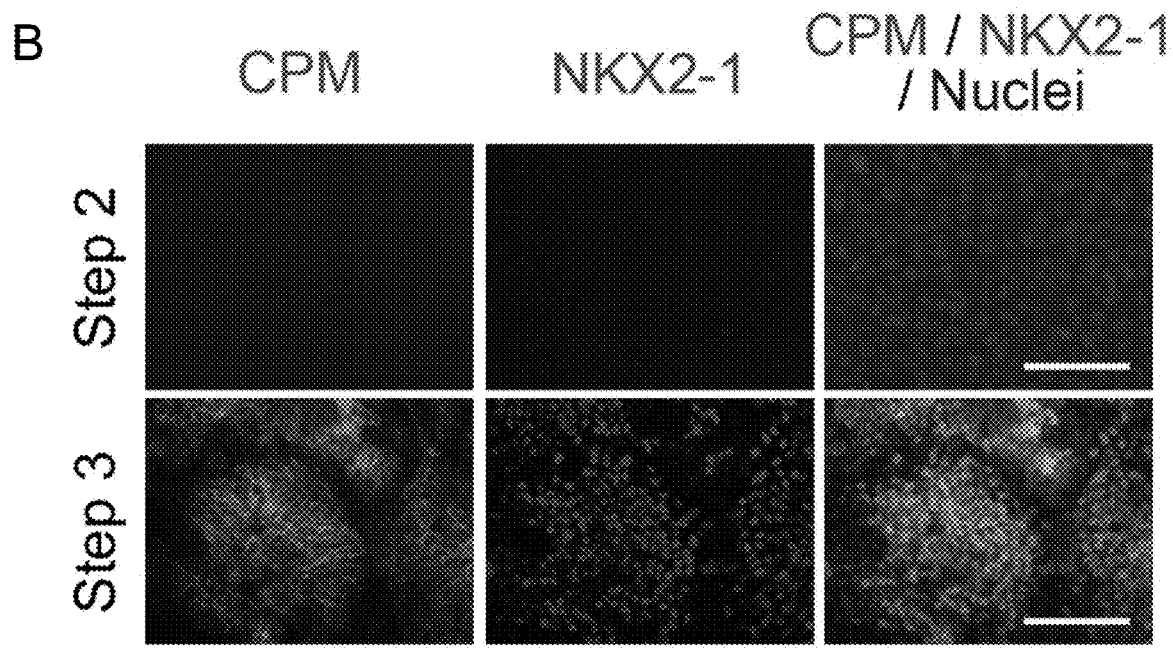

Fig. 3
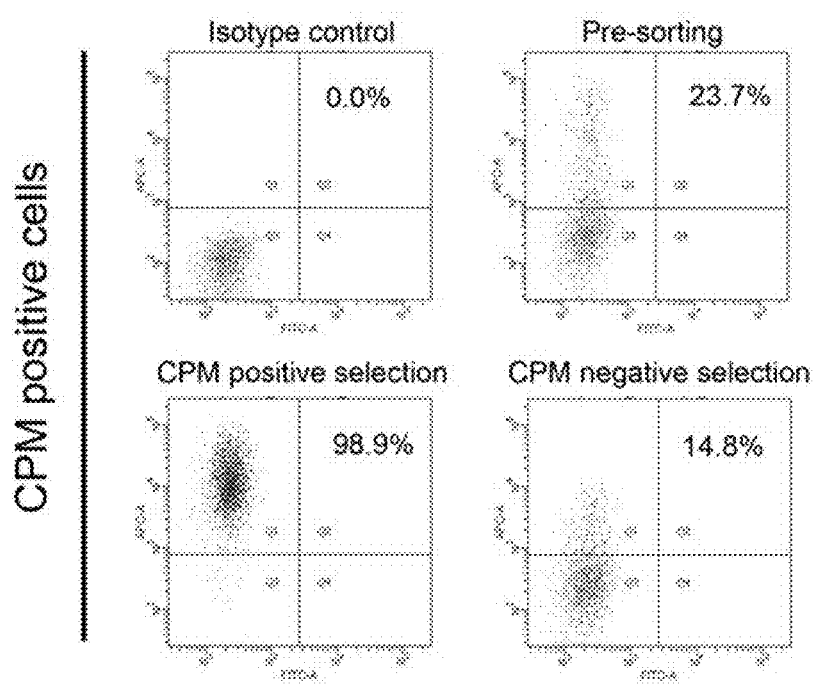
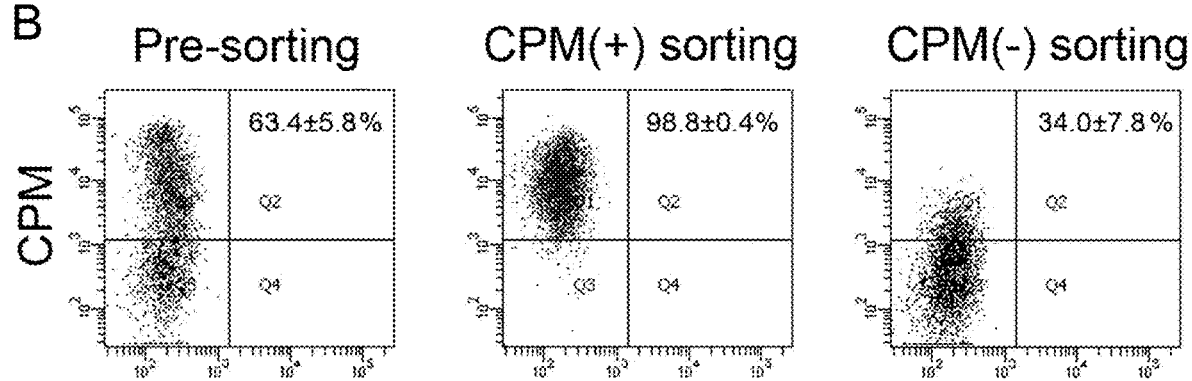

Fig. 14
A
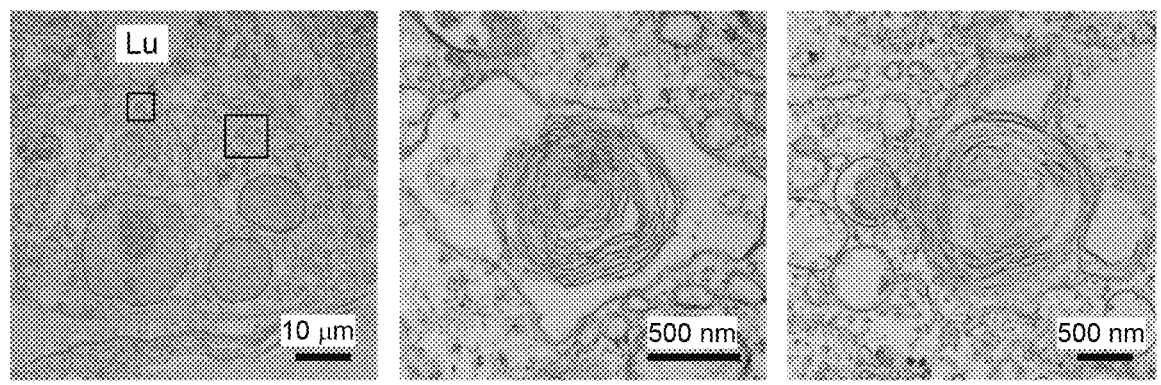
B
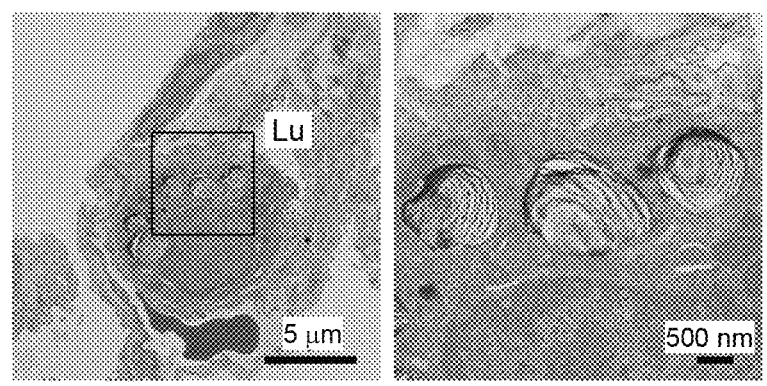
C
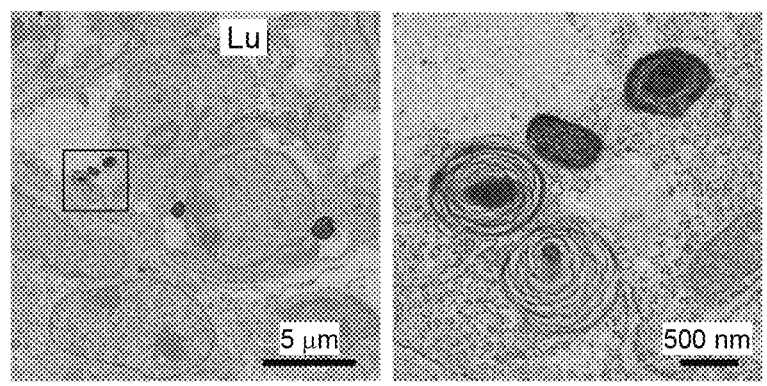

Fig. 15
A 3D culture derived from CPM+ cells CPM− cells
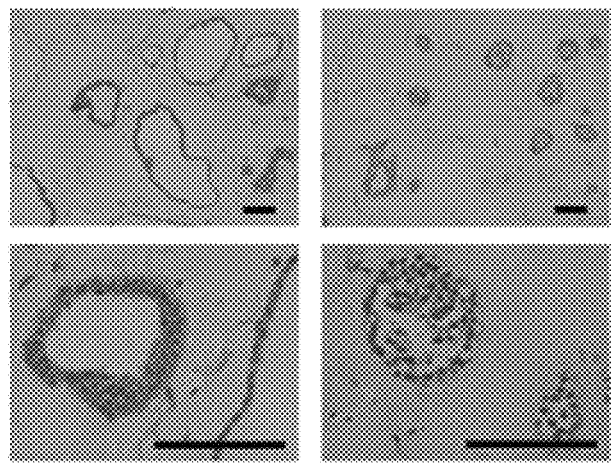
B
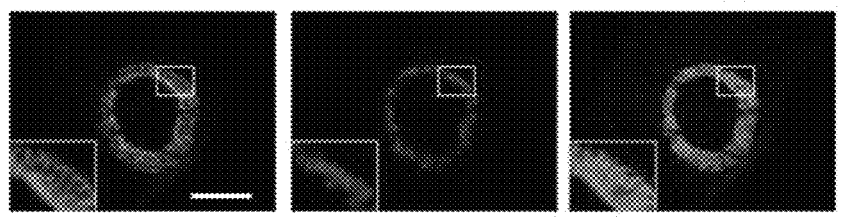
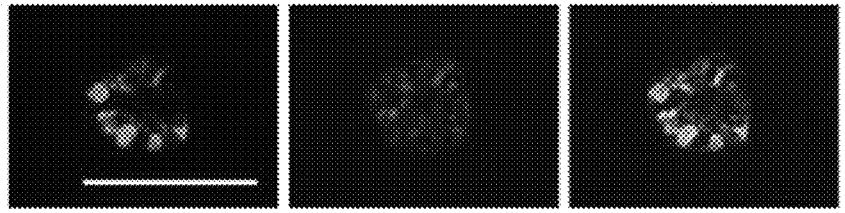
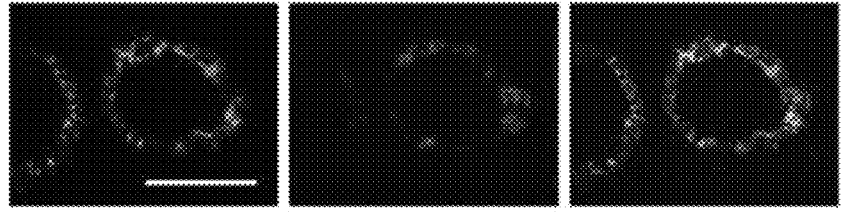

METHOD FOR INDUCING ALVEOLAR EPITHELIAL PROGENITOR CELLS

CROSS-REFERENCE TO RELATED APPLICATIONS

This application is a 371 of PCT/JP2014/061106, filed Apr. 14, 2014, which claims the benefit of Japanese Patent Application No. 2013-084034, filed Apr. 12, 2013.

TECHNICAL FIELD

The present invention relates to a method for producing alveolar epithelial progenitor cells from pluripotent stem cells. The present invention also relates to a kit used for producing alveolar epithelial progenitor cells from pluripotent stem cells.

BACKGROUND ART

The lung is one of the most complicated organs, and it is considered to be composed of approximately 40 different types of cells. Among them, the pulmonary alveolus is composed of the alveolar space, which stores gas, and the alveolar epithelium, which surrounds the same. In addition, the alveolar epithelium is composed of the type I alveolar epithelial cells and the type II alveolar epithelial cells. The former forms a blood-air barrier with the microvascular endothelium surrounding the pulmonary alveolus with the aid of the basal membrane and exchanges the intra-alveolar gas with the blood gas. The latter comprises many lamellar corpuscles, it undergoes exocytosis of pulmonary surfactants, and it forms the alveolar lining layer.

In recent years, cells having pluripotency, such as embryonic stem cells (ES cells) or induced pluripotent stem cells (iPS cells) obtained by introducing undifferentiated-cell-specific genes into somatic cells, have been reported (U.S. Pat. No. 5,843,780 and WO 2007/069666), methods for inducing alveolar epithelial cells from such cells have been reported (Rippon H. J. et al, Cloning Stem Cells 6: 49-56, 2004; Coraux C. et al, Am. J. Respir. Cell Mol. Biol., 32:87-92, 2005; and Morrisey E. E and Hogan B. L., Dev. Cell., 18: 8-23, 2010), and growth factors and the like that are necessary for the induction of such cells have also been reported. However, there are no examples demonstrating the efficient induction of human pulmonary alveolar cells.

Examples of diseases that destroy the pulmonary alveolus include emphysema, interstitial pneumonia, and lymphangioleiomyomatosis. In particular, emphysema is treated via symptomatic treatment or conservative treatment at present, and there is no radical treatment therefor. In addition, there is no radical treatment available for other pulmonary alveolar diseases, and the development of cell-transfer treatment has been accordingly awaited.

SUMMARY OF THE INVENTION

It is an object of the present invention to provide a method for producing alveolar epithelial progenitor cells from pluripotent stem cells. It is another object of the present invention to provide a kit used for producing alveolar epithelial progenitor cells from pluripotent stem cells.

The present inventors have conducted concentrated studies in order to attain the above objects. As a result, they discovered that pluripotent stem cells could be induced to differentiate into alveolar epithelial progenitor cells with the use of various growth factors and compounds. This has led to the completion of the present invention.

Specifically, the present invention includes the following.

[1] A method for producing alveolar epithelial progenitor cells from pluripotent stem cells comprising Steps (1) to (3) below:
 (1) culturing pluripotent stem cells in a medium containing activin A and a GSK3β inhibitor;
 (2) culturing the cells obtained in Step (1) in a medium containing a BMP inhibitor and a TGFβ inhibitor; and
 (3) culturing the cells obtained in Step (2) in a medium containing BMP4, retinoic acid, and a GSK3β inhibitor.

[2] The method according to [1], which further comprises a step of extracting CPM-positive cells as alveolar epithelial progenitor cells, following Step (3).

[3] The method according to [1] or [2], wherein Step (1) further comprises culturing pluripotent stem cells with the addition of an ROCK inhibitor and/or HDAC inhibitor to a medium.

[4] The method according to any one of [1] to [3], wherein Step (1) comprises culturing for 6 days or longer.

[5] The method according to any one of [1] to [4], wherein Step (2) comprises culturing for 4 days or longer.

[6] The method according to any one of [1] to [5], wherein Step (3) comprises culturing for 4 days or longer.

[7] The method according to any one of [1] to [6], wherein the GSK3β inhibitor is CHIR99021, the BMP inhibitor is Noggin, and the TGFβ inhibitor is SB431542.

[8] The method according to any one of [3] to [7], wherein the ROCK inhibitor is Y-27632 and/or the HDAC inhibitor is sodium butyrate.

[9] The method according to any one of [1] to [8], which further comprises Steps (4) and (5), following Step (3) below:
 (4) culturing the cells obtained in Step (3) in a medium containing FGF10; and
 (5) culturing the cells obtained in Step (4) in a medium containing a steroid drug, a cAMP derivative, a phosphodiesterase inhibitor, and KGF.

[10] The method according to [9], which further comprises a step of extracting CPM-positive cells as alveolar epithelial progenitor cells, following Step (5).

[11] The method according to [9] or [10], wherein Step (4) comprises culturing for 7 days or longer.

[12] The method according to any one of [9] to [11], wherein Step (5) comprises culturing for 4 days or longer.

[13] The method according to any one of [9] to [12], wherein the steroid drug is dexamethasone, the cAMP derivative is 8Br-cAMP, and the phosphodiesterase inhibitor is 3-isobutyl-1-methylxanthine (IBMX).

[14] The method according to any one of [1] to [13], wherein the alveolar epithelial progenitor cells are human alveolar epithelial progenitor cells.

[15] A method for producing alveolar epithelial progenitor cells, which further comprises a step of three-dimensional culture of the alveolar epithelial progenitor cells produced by the method according to [1] or [2].

[16] Alveolar epithelial progenitor cells produced by the method according to any one of [1] to [15].

[17] A kit used for producing alveolar epithelial progenitor cells from pluripotent stem cells, which comprises activin A, a GSK3β inhibitor, a BMP inhibitor, a TGFβ inhibitor, BMP4, retinoic acid, a steroid drug, a cAMP derivative, a phosphodiesterase inhibitor, FGF10, and KGF.

[18] The kit according to [17], which further comprises an ROCK inhibitor and/or HDAC inhibitor.

[19] The kit according to [17] or [18], wherein the GSK3β inhibitor is CHIR99021, the BMP inhibitor is Noggin, the TGFβ inhibitor is SB431542, the steroid drug is dexamethasone, the cAMP derivative is 8Br-cAMP, and the phosphodiesterase inhibitor is IBMX.

[20] The kit according to [18] or [19], wherein the ROCK inhibitor is Y-27632 and/or the HDAC inhibitor is sodium butyrate.

[21] A method for extracting alveolar epithelial progenitor cells, which comprises a step of extracting CPM-positive cells as alveolar epithelial progenitor cells from a cell population including alveolar epithelial progenitor cells.

This description includes part or all of the content as disclosed in the description and/or drawings of Japanese Patent Application No. 2013-084034, which is a priority document of the present application.

BRIEF DESCRIPTION OF THE DRAWINGS

FIG. 1A and FIG. 1B each show a scheme for producing alveolar epithelial progenitor cells from pluripotent stem cells. In the figures, "Stage I" is synonymous with "Step 1," "Stage II" is synonymous with "Step 2," "Stage III" is synonymous with "Step 3," "Stage IV" is synonymous with "Step 4," and "Stage V" is synonymous with "Step 5." Hereafter, such "stages" and "steps" are collectively referred to as "Steps."

FIG. 2A shows images of immunostained CPM and NKX2-1 in the cells after the completion of Step 3. FIG. 2B shows images of immunostained CPM and NKX2-1 in the cells after the completion of Step 2 (upper images) and Step 3 (lower images).

FIG. 3A shows percentages of CPM-positive cells after sorting via CPM-based MACS, after the completion of Step 3. In the figure, "Isotype control" shows the results for the negative control, "Pre-sorting" shows the results for the cells before sorting via MACS, "CPM positive selection" shows the results for CPM-positive cells after sorting via MACS, and "CPM negative selection" shows the results for CPM-negative cells after sorting via MACS. FIG. 3B shows percentages of CPM-positive cells after sorting via CPM-based MACS after the completion of Step 3. "Pre-sorting" shows the results for the cells before sorting via MACS, "CPM(+) sorting" shows the results for the MACS-sorted CPM-positive cells, and "CPM(−) sorting" shows the results for the MACS-sorted CPM-negative cells.

FIG. 14A shows transmission electron microscopic images of spheroids following the three-dimensional culture of the CPM-positive cells after the completion of Step 3. In FIG. 14A, the images at the center and on the right are each an enlarged view of a part of the image on the left. FIG. 14B shows transmission electron microscopic images of type II alveolar epithelial cells of mouse lungs. The image on the right shows an enlarged view of a part of the image on the left. FIG. 14C shows transmission electron microscopic images of the mouse fetal lung at E17.5. The image on the right shows an enlarged view of a part of the image on the left. In the figures, "Lu" indicates a lumen.

FIG. 15A shows hematoxylin-eosin-stained images of the three-dimensionally cultured CPM-positive cells (left) and CPM-negative cells (right) after the completion of Step 3.

The lower images show enlarged views of the upper images. FIG. 15B shows images of the spheroids immunostained with the CPM, NKX2-1, GFP (SFTPC), SFTPC (endogenous), and AQP5 antibodies following the three-dimensional culture of the CPM-positive cells after the completion of Step 3.

EMBODIMENTS FOR CARRYING OUT THE INVENTION

Figure 4:
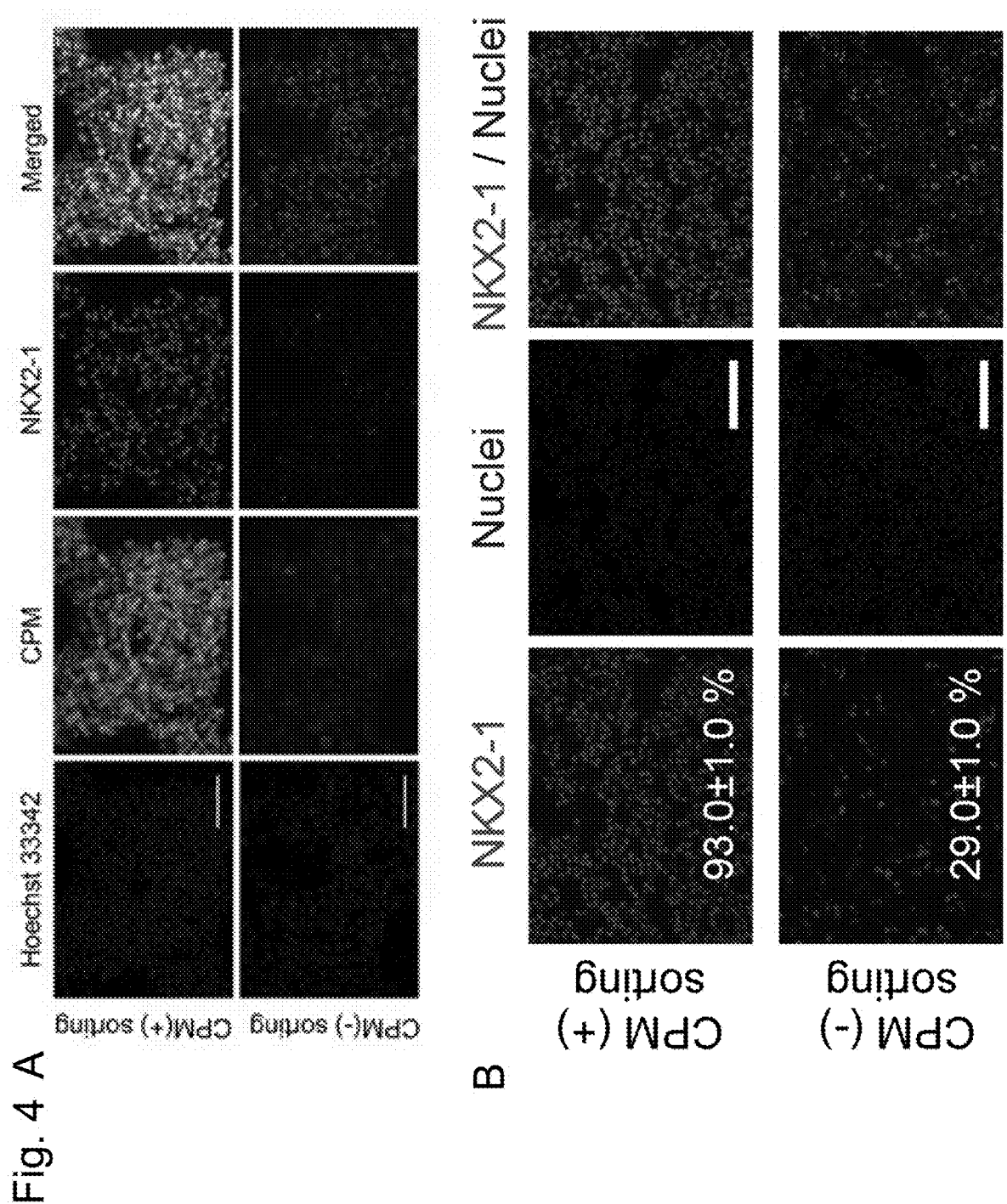
FIG. 4A shows images of immunostained CPM and NKX2-1 in the MACS-sorted CPM-positive cells (CPM(+) sorting) and in the CPM-negative cells (CPM(−) sorting) after the completion of Step 3.
FIG. 4B shows images of immunostained NKX2-1 in the MACS-sorted CPM-positive cells (CPM(+) sorting) and in the CPM-negative cells (CPM(−) sorting) after the completion of Step 3.

Hereafter, the present invention is described in detail.

The present invention provides a method for producing alveolar epithelial progenitor cells (e.g., human alveolar epithelial progenitor cells) from pluripotent stem cells comprising steps of culturing pluripotent stem cells in (1) a medium containing activin A and a GSK3β inhibitor, (2) a medium containing a BMP inhibitor and a TGFβ inhibitor, and (3) a medium containing BMP4, retinoic acid, and a GSK3β inhibitor.

The method for producing alveolar epithelial progenitor cells according to the present invention may comprise a step of extracting CPM-positive cells as the alveolar epithelial progenitor cells, following Step (3).

The method for producing alveolar epithelial progenitor cells according to the present invention may further comprise Step (4) of culture in a medium containing FGF10 and Step (5) of culture in a medium containing a steroid drug, a cAMP derivative, a phosphodiesterase inhibitor, and KGF, following Step (3). In addition, the method may further comprise a step of extracting CPM-positive cells as the alveolar epithelial progenitor cells, following Step (5).

In the present invention, the term "alveolar epithelial progenitor cells" refers to progenitor cells of type I alveolar epithelial cells or type II alveolar epithelial cells, which express CPM or NKX2-1. In this description, the term "alveolar epithelial cells" is not distinguished from the term "alveolar epithelial progenitor cells," unless otherwise specified. In the present invention, "CPM" indicates a polynucleotide shown in the NCBI Accession Number NM_001005502, NM_001874, or NM_198320 or a protein encoded thereby. In the present invention, "NKX2-1" indicates a polynucleotide shown in the NCBI Accession Number NM_001079668 or NM_003317 or a protein encoded thereby.

In the present invention, examples of markers for alveolar epithelial progenitor cells include polynucleotides selected from the group consisting of SFTPB (NCBI Accession Numbers NM_000542 and NM_198843), SFTPC (NCBI Accession Numbers NM_001172357, NM_001172410, and NM_003018), and CCSP (NCBI Accession Number NM_003357) and proteins encoded by such polynucleotides.

[Step of Culture in a Medium Containing Activin A and a GSK3β Inhibitor]

A medium used in the step of culturing pluripotent stem cells according to the present invention can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. RPMI 1640 medium supplemented with B27 and antibiotics is preferable.

In this step, pluripotent stem cells are cultured in a medium prepared by supplementing the basal medium described above with activin A and a GSK3β inhibitor. In this step, an HDAC inhibitor may further be added.

Activin A is a homodimer with two beta A chains, the amino acid sequence of activin A is 100% homologous to that of a protein of a human, mouse, rat, pig, cow, or cat, and, accordingly, the relevant species are not particularly limited. In the present invention, activin A is preferably of an active form with the N-terminal peptide being cleaved, and it is preferably a homodimer comprising, bound thereto via a disulfide bond, the Gly311-Ser426 fragment with the N-terminal peptide of the inhibin beta A chain (e.g., NCBI Accession Number NP_002183) being cleaved. Such activin A is commercially available from, for example, Wako and R&D Systems.

The activin A concentration in the medium is, for example, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, 300 ng/ml, 400 ng/ml, 500 ng/ml, 600 ng/ml, 700 ng/ml, 800 ng/ml, 900 ng/ml, or 1 mg/ml, although the concentration is not limited thereto. The concentration is preferably 100 ng/ml.

The term "GSK3β inhibitor" used herein is defined as a substance that inhibits kinase activity of the GSK-3β protein (e.g., the capacity for phosphorylation of β-catenin), and many such substances are already known. Examples thereof include: an indirubin derivative, such as BIO, which is also known as a GSK-3β inhibitor IX (6-bromoindirubin-3'-oxime); a maleimide derivative, such as SB216763 (3-(2,4-dichlorophenyl)-4-(1-methyl-1H-indol-3-yl)-1H-pyrrole-2,5-dione); a phenyl α-bromomethylketone compound, such as a GSK-3β inhibitor VII (4-dibromoacetophenone); a cell-membrane-permeable phosphorylated peptide, such as L803-mts, which is also known as a GSK-3β peptide inhibitor (i.e., Myr-N-GKEAPPAPPQSpP-NH$_2$); and CHIR99021, such as 6-[2-[4-(2,4-dichlorophenyl)-5-(4-methyl-1H-imidazol-2-yl)pyrimidin-2-ylamino]ethylamino]pyridine-3-carbonitrile, with high selectivity. While such compounds are commercially available from, for example, Calbiochem or Biomol, and easily used, such compounds may be obtained from other companies, or persons may prepare such compounds by themselves.

A GSK-3β inhibitor that can be preferably used in the present invention is CHIR99021. In this step, the concentration of CHIR99021 in a medium is, for example, 1 nM, 10 nM, 50 nM, 100 nM, 500 nM, 750 nM, 1 µM, 1.5 µM, 2 µM, 2.5 µM, 3 µM, 3.5 µM, 4 µM, 4.5 µM, 5 µM, 6 µM, 7 µM, 8 µM, 9 µM, 10 µM, 15 µM, 20 µM, 25 µM, 30 µM, 40 µM, or 50 µM, although the concentration is not limited thereto. In this step, the concentration is preferably 1 µM.

The term "HDAC inhibitor" is defined as a substance that inhibits or inactivates enzyme activity of histone deacetylase (HDAC). Examples thereof include low-molecular-weight inhibitors, such as valproic acid (VPA) (Nat. Biotechnol., 26 (7): 795-797, 2008), trichostatin A, sodium butyrate (NaB), MC 1293, and M344; nucleic acid-based expression inhibitors such as siRNAs and shRNAs against HDAC (e.g., HDAC1 siRNA Smartpool® (Millipore) and HuSH 29mer shRNA Constructs against HDAC1 (OriGene)); and DNA methyltransferase inhibitors (e.g., 5'-azacytidine) (Nat. Biotechnol., 26 (7): 795-797, 2008).

An HDAC inhibitor that can be preferably used in the present invention is sodium butyrate (NaB). The concentration of sodium butyrate (NaB) in a medium is, for example, 1 µM, 10 µM, 50 µM, 100 µM, 250 µM, 500 µM, 750 µM, 1 mM, 2 mM, 3 mM, 4 mM, or 5 mM, although the concentration is not limited thereto. The concentration is preferably 250 nM.

In this step, culture may be conducted in a culture vessel treated with a coating agent. A coating agent may be a naturally occurring or artificially synthesized extracellular matrix. Examples thereof include BD Matrigel, collagen, gelatin, laminin, heparan sulfate proteoglycan, entactin, and a combination of any thereof, with Matrigel being preferable.

This step may comprise a process of pluripotent stem cell detachment. Examples of methods for cell detachment include a method of mechanical detachment and a method of cell detachment involving the use of a cell detachment solution having protease activity and collagenase activity (e.g., Accutase™ and Accumax™) or a cell detachment solution having collagenase activity alone. It is preferable that human pluripotent stem cells be detached with the use of a cell detachment solution having protease activity and collagenase activity (and the use of Accutase™ is particularly preferable).

When the step comprises a process of cell detachment, an ROCK inhibitor may be added to a medium, so as to inhibit pluripotent stem cell death caused by detachment.

An ROCK inhibitor is not particularly limited, provided that it can inhibit functions of Rho kinase (ROCK). Examples thereof include: Y-27632 ((+)-(R)-trans-4-(1-aminoethyl)-N-(4-pyridyl)cyclohexanecarboxamide dihydrochloride) (e.g., Ishizaki et al., Mol. Pharmacol., 57, 976-983, 2000; Narumiya et al., Methods Enzymol., 325, 273-284, 2000); Fasudil/HA1077 (e.g., Uenata et al., Nature 389: 990-994, 1997); H-1152 (e.g., Sasaki et al., Pharmacol. Ther., 93: 225-232, 2002); Wf-536 (e.g., Nakajima et al., Cancer Chemother. Pharmacol., 52 (4): 319-324, 2003) and derivatives thereof; antisense nucleic acids against ROCK; RNA interference-inducible nucleic acids (e.g., siRNA); dominant-negative variants; and expression vectors thereof. Since other low-molecular-weight compounds are known as ROCK inhibitors, such compounds and derivatives thereof can also be used in the present invention (e.g., U.S. Patent Application Publication Nos. 2005/0209261, 2005/0192304, 2004/0014755, 2004/0002508, 2004/0002507, 2003/0125344, and 2003/0087919, WO 2003/062227, WO 2003/059913, WO 2003/062225, WO 2002/076976, and WO 2004/039796). In the present invention, one or more types of ROCK inhibitors can be used.

An ROCK inhibitor that can be preferably used in the present invention is Y-27632. The Y-27632 concentration is, for example, 100 nM, 500 nM, 750 nM, 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, or 50 µM, although the concentration is not limited thereto. The concentration is preferably 10 µM.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period may be at least 3 days, 4 days, 5 days, 6 days, 7 days, 8 days, 9 days, 10 days, 11 days, or 12 days. The culture period is preferably at least 6 days, and it is particularly preferably 6 days. When the ROCK inhibitor is added, the duration of addition is 1 day or 2 days, with 1 day being preferable. When the HDAC inhibitor is further added, the addition is initiated on the day following the initiation of the step, and culture is conducted for at least 3 days, 4 days, 5 days, 6 days, 7 days, 8 days, 9 days, 10 days, or 11 days. Culture is preferably conducted for at least 5 days, and particularly preferably for 5 days, in the presence of the HDAC inhibitor.

[Step of Culture in a Medium Containing BMP Inhibitor and TGFβ Inhibitor]

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with Glutamax, B27, N2,3'-thiol glycerol, and ascorbic acid is preferable.

In this step, the cells obtained in the previous step (i.e., the step of culture of pluripotent stem cells in a medium containing activin A and a GSK3β inhibitor) are cultured in a medium prepared by supplementing the basal medium with a BMP inhibitor and a TGFβ inhibitor.

Examples of BMP inhibitors include: protein-based inhibitors, such as Chordin, Noggin, and Follistatin; dorsomorphin (i.e., 6-[4-(2-piperidin-1-yl-ethoxy)phenyl]-3-pyridin-4-yl-pyrazolo[1,5-a]pyrimidine) and a derivative thereof (P. B. Yu et al., 2007, Circulation, 116: II_60; P. B. Yu et al., 2008, Nat. Chem. Biol., 4:33-41; J. Hao et al., 2008, PLoS ONE, 3 (8): e2904); and LDN-193189 (i.e., 4-(6-(4-(piperazin-1-yl)phenyl)pyrazolo[1,5-a]pyrimidin-3-yl)quinoline). Dorsomorphin and LDN-193189 are commercially available from Sigma-Aldrich and Stemgent, respectively.

A BMP inhibitor that can be preferably used in the present invention is Noggin. The concentration of Noggin in a medium is not particularly limited, provided that BMP can be inhibited. For example, such concentration is 1 ng/ml, 10 ng/ml, 50 ng/ml, 100 ng/ml, 200 ng/ml, 30 ng/ml, 400 ng/ml, 50 ng/ml, 600 ng/ml, 700 ng/ml, 800 ng/ml, 900 ng/ml, 1 µg/ml, or 2 µg/ml, although the concentration is not limited thereto. The concentration is preferably 200 ng/ml.

The term "TGFβ inhibitor" used herein refers to a substance that inhibits signal transmission from the binding of TGFβ to a receptor leading to SMAD. A TGFβ inhibitor is not particularly limited, provided that such substance inhibits TGFβ from binding to a receptor; i.e., the ALK family, or such substance inhibits phosphorylation of SMAD caused by the ALK family. Examples thereof include Lefty-1 (e.g., NCBI Accession Nos. mouse NM_010094 and human NM_020997), SB431542 (4-(4-(benzo[d][1,3]dioxol-5-yl)-5-(pyridin-2-yl)-1H-imidazol-2-yl)benzamide), SB202190 (R. K. Lindemann, et al., Mol. Cancer, 2003, 2: 20), SB505124 (GlaxoSmithKline), NPC30345, SD093, SD908, SD208 (Scios), LY2109761, LY364947, LY580276 (Lilly Research Laboratories), A-83-01 (WO 2009/146408), and derivatives thereof.

A TGFβ inhibitor that can be preferably used in the present invention is SB431542. The SB431542 concentration in a medium is not particularly limited, provided that TGFβ is inhibited. For example, such concentration can be 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM, 60 µM, 70 µM, 80 µM, 90 µM, 100 µM, 200 µM, 300 µM, 400 µM, or 500 µM, although the concentration is not limited thereto. The concentration is preferably 10 µM.

In this step, culture may be conducted in a culture vessel treated with a coating agent. Examples of coating agents include BD Matrigel, collagen, gelatin, laminin, heparan sulfate proteoglycan, entactin, and a combination of any thereof, with Matrigel being preferable.

This step may be implemented by exchanging the cell culture medium obtained in the previous step with the medium described above. Alternatively, cells may be detached and reseeded in a culture vessel. When cells are to be detached, particular cells may be selected, and, for example, SOX17- and/or FOXA2-positive cells may be selected and used in this step. This method is preferably implemented by means of media exchange.

When the step comprises a process of cell detachment, an ROCK inhibitor may be added to a medium, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period may be at least 1 day, 2 days, 3 days, 4 days, 5 days, 6 days, 7 days, or 8 days. The culture period is preferably 4 days.

[Step of Culture in a Medium Containing BMP4, Retinoic Acid, and GSK3β Inhibitor]

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with Glutamax, B27, N2, 3'-thiol glycerol, and ascorbic acid is preferable.

In this step, the cells obtained in the previous step (i.e., the step of culture in a medium containing a BMP inhibitor and a TGFβ inhibitor) are cultured in a medium prepared by supplementing the basal medium with BMP4, retinoic acid, and a GSK3β inhibitor.

The term "BMP4" used herein refers to a protein encoded by the polynucleotide shown in the NCBI Accession Number NM_001202, NM_130850, or NM_130851, and it may be in an active form resulting from cleavage by a protease.

The BMP4 concentration in a medium is not particularly limited. For example, such concentration may be 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 µg/ml, although the concentration is not limited thereto. The concentration is preferably 100 ng/ml.

While all-trans retinoic acid (ATRA) is exemplified as retinoic acid, artificially modified retinoic acid that retains functions of naturally occurring retinoic acid may be used. Examples thereof include 4-[[(5,6,7,8-tetrahydro-5,5,8,8-tetramethyl-2-naphthalenyl)carbonyl]amino]-benzoic acid (AM580) (Tamura, K. et al., Cell Differ. Dev., 32: 17-26, 1990), 4-[(1E)-2-(5,6,7,8-tetrahydro-5,5,8,8-tetramethyl-2-naphthalenyl)-1-propen-1-yl]-benzoic acid (TTNPB) (Strickland, S., et al., Cancer Res., 43: 5268-5272, 1983), retinol palmitate, retinol, retinal, 3-dehydroretinoic acid, 3-dehydroretinol, 3-dehydroretinal, and compounds described in Abe, E., et al., Proc. Natl. Acad. Sci., (U.S.A.) 78: 4990-4994, 1981; Schwartz, E. L. et al., Proc. Am. Assoc. Cancer Res., 24: 18, 1983; Tanenaga, K. et al., Cancer Res., 40: 914-919, 1980.

The retinoic acid concentration in a medium is not particularly limited. For example, such concentration can be 1 nM, 5 nM, 10 nM, 15 nM, 20 nM, 25 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, or 1 µM, although the concentration is not limited thereto. The concentration is preferably 50 nM.

The GSK3β inhibitor as described above can be used in this step, and the GSK3β inhibitor is preferably CHIR99021. In this step, the CHIR99021 concentration in a medium is, for example, 1 nM, 10 nM, 50 nM, 100 nM, 500 nM, 750 nM, 1 µM, 1.5 µM, 2 µM, 2.5 µM, 3 µM, 3.5 µM, 4 µM, 4.5 µM, 5 µM, 6 µM, 7 µM, 8 µM, 9 µM, 10 µM, 15 µM, 20 µM, 25 µM, 30 µM, 40 µM, or 50 µM, although the concentration is not limited thereto. In this step, the concentration is preferably 2.5 µM.

In this step, culture may be conducted in a culture vessel treated with a coating agent. A coating agent may be a naturally occurring or artificially synthesized extracellular matrix. Examples thereof include BD Matrigel, collagen, gelatin, laminin, heparan sulfate proteoglycan, entactin, and a combination of any thereof, with Matrigel being preferable.

This step may be implemented by exchanging the cell culture medium obtained in the previous step with the medium described above. Alternatively, cells may be detached and reseeded in a culture vessel. When cells are to be detached, particular cells may be selected, and, for example, SOX2-, SOX17-, and/or FOXA2-positive cells may be selected and used in this step. This method is preferably implemented by means of media exchange.

When the step comprises a process of cell detachment, an ROCK inhibitor may be added to a medium, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period may be at least 1 day, 2 days, 3 days, 4 days, 5 days, 6 days, 7 days, or 8 days. The culture period is preferably at least 4 days, and more preferably 4 days.

[Step of Culture in a Medium Containing FGF10]

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. A medium mixture of DMEM and Ham's F12 supplemented with Glutamax, B27, N2,3'-thiol glycerol, and ascorbic acid is preferable.

In this step, the cells obtained in the previous step (i.e., the step of culture in a medium containing BMP4, retinoic acid, and a GSK3β inhibitor) are cultured in a medium prepared by supplementing the basal medium with FGF10.

The term "FGF10" used herein refers to a protein encoded by the polynucleotide shown in the NCBI Accession Number NM_004465, and it may be in an active form resulting from cleavage by a protease. Such FGF10 is commercially available from, for example, Life Technologies or Wako.

The FGF10 concentration in a medium is not particularly limited. For example, such concentration may be 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 µg/ml, although the concentration is not limited thereto. The concentration is preferably 100 ng/ml.

In this step, culture may be conducted in a culture vessel treated with a coating agent. A coating agent may be a naturally occurring or artificially synthesized extracellular matrix. Examples thereof include BD Matrigel, collagen, gelatin, laminin, heparan sulfate proteoglycan, entactin, and a combination of any thereof, with Matrigel being preferable.

This step may be implemented by exchanging the cell culture medium obtained in the previous step with the medium described above. Alternatively, cells may be detached and reseeded in a culture vessel. When cells are to be detached, particular cells may be selected, and, for example, NKX2-1- and/or FOXA2-positive cells may be selected and used in this step. This method is preferably implemented by means of media exchange.

When the step comprises a process of cell detachment, an ROCK inhibitor may be added to a medium, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period may be at least 3 days, 4 days, 5 days, 6 days, 7 days, 8 days, 9 days, 10 days, 11 days, 12 days, 13 days, or 14 days. The culture period is preferably at least 7 days, and more preferably 7 days.

[Step of Culture in a Medium Containing a Steroid Drug, a cAMP Derivative, a Phosphodiesterase Inhibitor, and KGF]

A medium used in this step can be prepared from a medium used for animal cell culture as a basal medium. Examples of basal media include IMDM medium, Medium 199, Eagle's Minimum Essential Medium (EMEM), αMEM medium, Dulbecco's modified Eagle's Medium (DMEM), Ham's F12 medium, RPMI 1640 medium, Fischer's medium, Neurobasal Medium (Life Technologies), and a mixture of any such media. A medium may or may not contain blood serum. A medium may optionally contain one or more serum substitutes selected from among, for example, albumin, transferrin, Knockout Serum Replacement (KSR) (an FBS serum substitute used for ES cell culture), N2 supplements (Invitrogen), B27 supplements (Invitrogen), fatty acid, insulin, ITS Premix, collagen precursors, trace elements, 2-mercaptoethanol, and 3'-thiol glycerol. In addition, a medium can contain one or more substances selected from among, for example, lipids, amino acids, L-glutamine, Glutamax (Invitrogen), nonessential amino acids, vitamins, growth factors, low-molecular-weight compounds, antibiotics, antioxidants, pyruvic acids, buffer agents, and inorganic salts. Ham's F12 medium containing albumin, buffer agents (e.g., HEPES), calcium chloride, ITS Premix, and antibiotics is preferable.

In this step, the cells obtained in the previous step (i.e., the step of culture in a medium containing FGF10) are cultured in a medium prepared by supplementing the basal medium with a steroid drug, a cAMP derivative, a phosphodiesterase inhibitor, and KGF.

The term "steroid drug" used herein refers to a steroidal anti-inflammatory drug, such as glucocorticoid or a synthetic derivative thereof. Specific examples thereof include hydrocortisone, hydrocortisone succinate, prednisolone, methylprednisolone, methylprednisolone succinate, triamcinolone, triamcinolone acetonide, dexamethasone, and betamethasone.

A steroid drug that can be preferably used in the present invention is dexamethasone. The dexamethasone concentration in a medium is not particularly limited. For example, such concentration may be 1 nM, 5 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, or 1 µM, although the concentration is not limited thereto. The concentration is preferably 50 nM.

The term "cAMP derivative" used herein refers to a compound with a modified cyclic AMP substituent. Examples thereof include cyclic adenosine monophosphate (cAMP), 8-bromo cyclic adenosine monophosphate (8-Br-cAMP or 8Br-cAMP), 8-chloro-cyclic adenosine monophosphate (8-Cl-cAMP), 8-(4-chlorophenylthio)cyclic adenosine monophosphate (8-CPT-cAMP), and dibutyryl cyclic adenosine monophosphate (DB-cAMP).

A cAMP derivative that can be preferably used in the present invention is 8-Br-cAMP. The concentration of 8-Br-cAMP in a medium is not particularly limited. For example, such concentration can be 1 µM, 5 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, or 1 mM, although the concentration is not limited thereto. The concentration is preferably 100 µM.

The term "phosphodiesterase inhibitor" used herein refers to a compound that inhibits phosphodiesterase (PDE), so as to increase the concentration of cAMP or cGMP in the cells. Examples thereof include 1,3-dimethylxanthine, 6,7-dimethoxy-1-(3,4-dimethoxybenzyl)isoquinoline, 4-{[3',4'-(methylenedioxy)benzyl]amino}-6-methoxyquinazoline, 8-methoxymethyl-3-isobutyl-1-methylxanthine, and 3-isobutyl-1-methylxanthine (IBMX).

A phosphodiesterase inhibitor that can be preferably used in the present invention is IBMX. The IBMX concentration in a medium is not particularly limited. For example, such concentration can be 1 µM, 5 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, or 1 mM, although the concentration is not limited thereto. The concentration is preferably 100 nM.

The term "KGF" used herein refers to a protein encoded by the polynucleotide shown in the NCBI Accession Number NM_002009, and it may be in an active form resulting from cleavage by a protease. Such KGF is commercially available from, for example, Wako.

The concentration of KGF in a medium is not particularly limited. For example, such concentration can be 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 200 ng/ml, 300 ng/ml, 400 ng/ml, 500 ng/ml, 600 ng/ml, 700 ng/ml, 800 ng/ml, 900 ng/ml, or 1 µg/ml, although the concentration is not limited thereto. The concentration is preferably 100 ng/ml.

In this step, culture may be conducted in a culture vessel treated with a coating agent. A coating agent may be a naturally occurring or artificially synthesized extracellular matrix. Examples thereof include BD Matrigel, collagen, gelatin, laminin, heparan sulfate proteoglycan, entactin, and a combination of any thereof, with Matrigel being preferable.

This step may be implemented by exchanging the cell culture medium obtained in the previous step with the medium described above. Alternatively, cells may be detached and reseeded in a culture vessel. When cells are to be detached, particular cells may be selected, and, for example, NKX2-1-positive cells may be selected and used in this step. This method is preferably implemented by means of media exchange.

When the step comprises a process of cell detachment, an ROCK inhibitor may be added to a medium, so as to inhibit pluripotent stem cell death caused by detachment.

Concerning culture conditions, culture is conducted at about 30° C. to 40° C., and preferably at about 37° C., although the temperature is not limited thereto. Culture is conducted under an atmosphere of air containing $CO_2$, and the $CO_2$ concentration is preferably about 2% to 5%.

The culture period is not particularly limited because long-term culture would not cause any problems. For example, the culture period may be at least 1 day, 2 days, 3 days, 4 days, 5 days, 6 days, 7 days, or 8 days. The culture period is preferably at least 4 days, and it is more preferably 4 days.

[Three-Dimensional Culture]

The present invention provides a method for three-dimensional culture of alveolar epithelial progenitor cells for further maturation of alveolar epithelial progenitor cells. According to the present invention, three-dimensional culture is carried out by subjecting cells to float culture in the form of cell masses (i.e., spheroids). According to the present invention, three-dimensional culture can be carried out with the use of, for example, Cell Culture Inserts provided by BD.

According to the present invention, three-dimensional culture may be conducted in the presence of other cell species. Examples of other cell species that may be used include human pulmonary fibroblasts and human fetal pulmonary fibroblasts. Such cells are commercially available from, for example, American Type Culture Collection (ATCC) and DV Biologics.

The medium used for three-dimensional culture according to the present invention may be a medium that is used in the step of culture conducted in a medium containing a steroid drug, a cAMP derivative, a phosphodiesterase inhibitor, and KGF. Use of a medium supplemented with an extracellular matrix may be preferable. The ratio of the volume of the extracellular matrix to the volume of the medium is not particularly limited. For example, these substances can be mixed at a ratio of 5:1, 4:1, 3:1, 2:1, 1:1, 1:2, 1:3, 1:4, or 1:5. In the present invention, an extracellular matrix is a supramolecular structure that exists outside the cell, and it may be a naturally occurring or artificial (recombinant) structure. Examples thereof include substances such as collagen, proteoglycan, fibronectin, hyaluronic acid, tenascin, entactin, elastin, fibrillin, and laminin, and fragments thereof. These extracellular matrices may be used in combination. For example, extracellular matrices may be prepared from cells such as BD Matrigel™. An example of an artificial structure is a laminin fragment.

The period for three-dimensional culture is not particularly limited because long-term culture would not cause any problems. For example, the culture period may be at least 5 days, 6 days, 7 days, 8 days, 9 days, 10 days, 11 days, or 12 days. The culture period is preferably at least 10 days, and particularly preferably 10 days, 11 days, or 12 days.

[Pluripotent Stem Cells]

Pluripotent stem cells that can be used in the present invention are stem cells that have the potential to differentiate into any types of cells existing in organisms (i.e., pluripotency) and have the potential to grow. Examples thereof include embryonic stem cells (ES cells), nuclear transfer-derived embryonic stem cells from cloned embryos (ntES cells), germline stem cells (GS cells), embryonic germ cells (EG cells), induced pluripotent stem cells (iPS cells), and pluripotent cells derived from cultured fibroblasts and myeloid stem cells (Muse cells). In the present invention, the use of iPS cells or Muse cells is preferable because cells of interest can be obtained without destroying embryos.

(A) Embryonic Stem Cells

ES cells are pluripotent stem cells having the potential to grow through autoreproduction, and they are established from embryoblasts of early embryos (e.g., blastocysts) of mammalians such as humans or mice.

ES cells are embryo-derived stem cells originating from embryoblasts of blastocysts, which are embryos after the 8-cell stage and the morula stage of fertilized eggs. Such ES cells have the potential to differentiate into any types of cells constituting an adult; that is, so-called pluripotency and potential to grow through autoreproduction. ES cells were discovered in mice in 1981 (M. J. Evans and M. H. Kaufman, 1981, Nature 292: 154-156). Thereafter, ES cells of primates, such as humans and monkeys, were also established (J. A. Thomson, et al., 1998, Science 282: 1145-1147; J. A. Thomson, et al., 1995, Proc. Natl. Acad. Sci., U.S.A., 92: 7844-7848; J. A. Thomson, et al., 1996, Biol. Reprod., 55: 254-259; J. A. Thomson and V. S. Marshall, 1998, Curr. Top. Dev. Biol., 38: 133-165).

ES cells can be established by extracting embryoblasts from blastocysts of fertilized eggs of target animals and culturing the embryoblasts in fibroblast feeders. Cells can be maintained via subculture with the use of a medium supplemented with substances such as leukemia inhibitory factors (LIF) and basic fibroblast growth factors (bFGF). Human and monkey ES cells can be established and maintained by the methods described in, for example, U.S. Pat. No. 5,843,780; Thomson J. A., et al., 1995, Proc. Natl. Acad. Sci., U.S.A., 92: 7844-7848; Thomson, J. A., et al., 1998, Science 282: 1145-1147; H. Suemori et al., 2006, Biochem. Biophys. Res. Commun., 345: 926-932; M. Ueno et al., 2006, Proc. Natl. Acad. Sci. U.S.A., 103:9554-9559; H. Suemori et al., 2001, Dev. Dyn., 222:273-279; H. Kawasaki et al., 2002, Proc. Natl. Acad. Sci. U.S.A., 99:1580-1585; and Klimanskaya I, et al., 2006, Nature 444: 481-485.

Human ES cells can be maintained with the use of a medium for the production of ES cells, such as a DMEM/F-12 medium supplemented with 0.1 mM 2-mercaptoethanol, 0.1 mM nonessential amino acids, 2 mM L-glutamic acid, 20% KSR, and 4 ng/ml bFGF, at 37° C. in the presence of 5% $CO_2$ in a moist atmosphere (H. Suemori, et al., 2006, Biochem. Biophys. Res. Commun., 345: 926-932). It is necessary that ES cells be subjected to subculture every 3 or 4 days. Subculture can be carried out with the use of 0.25% trypsin and 0.1 mg/ml collagenase IV in PBS containing 1 mM $CaCl_2$ and 20% KSR.

In general, ES cells can be selected via real-time PCR using the expression of a gene marker such as alkaline phosphatase, Oct-3/4, or Nanog as an indicator. When human ES cells are to be selected, in particular, the expression of a gene marker such as OCT-3/4, NANOG, or ECAD can be employed as an indicator (E. Kroon et al., 2008, Nat. Biotechnol., 26: 443-452).

Human ES cells (e.g., WA01 (H1) and WA09 (H9)) are available from the WiCell Research Institute, and KhES-1, KhES-2, and KhES-3 are available from the Institute for Frontier Medical Sciences, Kyoto University (Kyoto, Japan).

(B) Germline Stem Cells

Germline stem cells are spermary-derived pluripotent stem cells that serve as sources for spermatogenesis. As with the case of ES cells, germline stem cells can be differentiated into various types of cells. For example, germline stem cells may be implanted into mouse blastocysts, so that chimeric mice may be produced (M. Kanatsu-Shinohara et al., 2003, Biol. Reprod., 69: 12-616; K. Shinohara et al., 2004, Cell, 119: 1001-1012). Germline stem cells are capable of autoreproduction in a medium containing glial cell line-derived neurotrophic factors (GDNF). In addition, germline stem cells can be obtained by repeating subculture under the same culture conditions as with those used for ES cells (Masanori Takebayashi et al., 2008, Experimental Medicine, Vol. 26, No. 5 (extra edition), pp. 41-46, Yodosha, Tokyo, Japan).

(C) Embryonic Germ Cells

As with ES cells, embryonic germ cells are pluripotent cells that are established from primordial germ cells during the prenatal period. Embryonic germ cells can be established by culturing primordial germ cells in the presence of substances such as LIF, bFGF, or stem cell factors (Y. Matsui et al., 1992, Cell, 70: 841-847; J. L. Resnick et al., 1992, Nature, 359: 550-551).

(D) Induced Pluripotent Stem Cells

Induced pluripotent stem (iPS) cells can be prepared by introducing particular reprogramming factors into somatic cells in the form of DNA or proteins. iPS cells are artificial stem cells derived from somatic cells that have substantially the same properties as ES cells, such as pluripotency and potential to grow through autoreproduction (K. Takahashi and S. Yamanaka, 2006, Cell, 126: 663-676; K. Takahashi et al., 2007, Cell, 131: 861-872; J. Yu et al., 2007, Science, 318: 1917-1920; Nakagawa, M. et al., Nat. Biotechnol., 26: 101-106, 2008; WO 2007/069666). Reprogramming factors may be composed of genes that are expressed specifically in ES cells, gene products or non-cording RNA thereof, or genes that play key roles in maintenance of the undifferentiated state of ES cells, gene products or non-coding RNA thereof, or low-molecular-weight compounds. Examples of genes included in reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. Such reprogramming factors may be used alone or in combination. Examples of combinations of reprogramming factors are described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu D, et al., 2008, Nat. Biotechnol., 26: 795-797, Shi Y, et al., 2008, Cell Stem Cell, 2: 525-528, Eminli S, et al., 2008, Stem Cells, 26: 2467-2474, Huangfu D, et al., 2008, Nat. Biotechnol., 26: 1269-1275, Shi Y, et al., 2008, Cell Stem Cell, 3, 568-574, Zhao Y, et al., 2008, Cell Stem Cell, 3: 475-479, Marson A, 2008, Cell Stem Cell, 3, 132-135, Feng B., et al., 2009, Nat Cell Biol., 11: 197-203, R. L. Judson et al., 2009, Nat. Biotech., 27: 459-461, Lyssiotis C A, et al., 2009, Proc. Natl. Acad. Sci., U.S.A. 106: 8912-8917, Kim J B, et al., 2009, Nature, 461: 649-643, Ichida, J. K., et al., 2009, Cell Stem Cell, 5: 491-503, Heng J. C. et al., 2010, Cell Stem Cell, 6: 167-74, Han J, et al., 2010, Nature, 463: 1096-100, Mali P, et al., 2010, and Stem Cells, 28: 713-720, Maekawa M, et al., 2011, Nature, 474: 225-9.

Factors that are used to enhance cell establishment efficiency are within the scope of the reprogramming factors described above. Examples thereof include: histone deacetylase (HDAC) inhibitors, such as low-molecular-weight inhibitors, including valproic acid (VPA), trichostatin A, sodium butyrate, MC 1293, and M344, and nucleic acid-based expression inhibitors, including siRNAs and shRNAs against HDAC (e.g., HDAC1 siRNA Smartpool® (Millipore) and HuSH 29mer shRNA constructs against HDAC1 (OriGene)); MEK inhibitors (e.g., PD184352, PD98059, U0126, SL327, and PD0325901); glycogen synthase kinase-3 inhibitors (e.g., Bio and CHIR99021); DNA methyltransferase inhibitors (e.g., 5-azacytidine); histone methyltransferase inhibitors (e.g., low-molecular-weight inhibitors, such as BIX-01294, and nucleic acid-based expression inhibitors against Suv39h1, Suv39h2, SetDB1 and G9a, such as siRNAs and shRNAs); an L-channel calcium agonist (e.g., Bayk8644); butyric acid, TGFβ, and ALK5 inhibitors (e.g., LY364947, SB431542, 616453, and A-83-01); p53 inhibitors (e.g., siRNA and shRNA against p53); ARID3A inhibitors (e.g., siRNA and shRNA against ARID3A), miRNA, such as miR-291-3p, miR-294, miR-295, and mir-302, Wnt signaling (e.g., soluble Wnt3a), neuro-peptide Y, prostaglandins (e.g., prostaglandin E2 and prostaglandinJ2), hTERT, SV40LT, UTF1, IRX6, GLIS1, PITX2, and DMRTB1. Factors that are used for the improvement of established efficiency are not particularly distinguished from reprogramming factors.

When reprogramming factors are in the form of proteins, for example, they may be introduced into somatic cells by a technique such as lipofection, fusion with cell-permeable peptides (e.g., HIV-derived TAT and polyarginine), or microinjection.

In contrast, reprogramming factors in the form of DNA can be introduced into somatic cells by a technique involving the use of a vector such as a virus, plasmid, or artificial chromosome vector, lipofection, a technique involving the use of a liposome, or microinjection, for example. Examples of virus vectors include retrovirus vectors, lentivirus vectors (Cell, 126, pp. 663-676, 2006; Cell, 131, pp. 861-872, 2007; Science, 318, pp. 1917-1920, 2007), adenovirus vectors (Science, 322, 945-949, 2008), adeno-associated virus vectors, and Sendai virus vectors (WO 2010/008054). Examples of artificial chromosome vectors include human artificial chromosome (HAC) vectors, yeast artificial chromosome (YAC) vectors, and bacterial artificial chromosome (BAC, PAC) vectors. Plasmids for mammalian animal cells can be used (Science, 322: 949-953, 2008). Vectors can comprise regulatory sequences, such as promoters, enhancers, ribosome-binding sequences, terminators, or polyadenylation sites, so that nuclear reprogramming substances can express. In addition, vectors can comprise selection marker sequences, such as drug tolerance genes (e.g., kanamycin tolerance genes, ampicillin tolerance genes, and puromycin tolerance genes), thymidine kinase genes, or diphtheria toxin genes, and reporter gene sequences, such as green fluorescent proteins (GFP), β-glucuronidase (GUS), or FLAG, according to need. The vector may comprise LoxP sequences in positions downstream and upstream of a gene encoding an reprogramming factor or a gene encoding a promoter and an reprogramming factor binding thereto, so as to eliminate such gene after the vector is introduced into somatic cells.

When reprogramming factors are in the form of RNA, for example, they may be introduced into somatic cells by a technique such as lipofection or microinjection. Alternatively, RNA comprising 5-methylcytidine and pseudouridine (TriLink Biotechnologies) incorporated therein may be used, so as to suppress degradation (Warren L, 2010, Cell Stem Cell 7: 618-630).

Examples of culture media used for iPS cell induction include DMEM containing 10% to 15% FBS, a DMEM/F12 or DME medium (such medium may adequately contain, for example, LIF, penicillin/streptomycin, puromycin, L-glutamine, nonessential amino acids, and (3-mercaptoethanol), commercially available culture media (e.g., a medium for mouse ES cell culture; TX-WES medium, Thrombo X), a medium for primate ES cell culture (a medium for primate ES/iPS cell culture, ReproCELL Incorporated), and a serum-free medium (mTeSR, Stemcell Technology).

For example, somatic cells are brought into contact with reprogramming factors in a 10% FBS-containing DMEM or DMEM/F12 medium, culture is conducted at 37° C. in the presence of 5% $CO_2$ for about 4 to 7 days, and the cells are reseeded in feeder cells (e.g., mitomycin C-treated STO cells or SNL cells). Culture is reinitiated in a medium for bFGF-containing primate ES cell culture about 10 days after the somatic cells are first brought into contact with the reprogramming factors, and iPS-like colonies can then be formed at least about 30 to 45 days after such contact.

Alternatively, culture may be conducted in a 10% FBS-containing DMEM medium (this medium can further contain LIF, penicillin/streptomycin, puromycin, L-glutamine, nonessential amino acids, β-mercaptoethanol, or the like, according to need) in feeder cells (e.g., mitomycin C-treated STO cells or SNL cells) at 37° C. in the presence of 5% $CO_2$, and ES-like colonies can then be formed at least about 25 to 30 days later. Alternatively, use of the somatic cells to be reprogrammed instead of feeder cells is preferable (Takahashi K, et al., 2009, PLoS One, 4: e8067 or WO 2010/137746), or use of an extracellular matrix (e.g., laminin-5 (WO 2009/123349) and Matrigel (BD)) is preferable.

In addition, culture may be conducted with the use of a serum-free medium (Sun N, et al., 2009, Proc. Natl. Acad. Sci., U.S.A. 106: 15720-15725). In order to enhance cell establishment efficiency, iPS cells may be established under low-oxygen conditions (oxygen concentration of 0.1% to 15%) (Yoshida Y, et al., 2009, Cell Stem Cell, 5: 237-241 or WO 2010/013845).

During the culture, medium exchange is initiated 2 days after the initiation of culture, and the medium is exchanged with fresh medium once a day. The number of somatic cells used for nuclear reprogramming is not limited, and it is about $5\times10^3$ to about $5\times10^6$ cells per 100 cm' of a culture dish.

iPS cells can be selected in accordance with the configuration of the formed colonies. When drug tolerance genes that express in association with genes that express upon reprogramming of somatic cells (e.g., Oct3/4 and Nanog) are introduced as marker genes, in contrast, culture can be conducted in a medium containing corresponding drugs (i.e., a selection medium). Thus, established iPS cells can be selected. When marker genes are fluorescent protein genes, fluorescent microscopic observation may be carried out. When marker genes are luminescent enzyme genes, luminescent substrates may be added. When marker genes are chromogenic enzyme genes, chromogenic substrates may be added. Thus, iPS cells can be selected.

The term "somatic cells" used herein refers to any animal cells except for germline cells or pluripotent cells such as egg cells, oocytes, and ES cells (preferably mammalian animal cells, including those of humans). Examples of somatic cells include, but are not limited to, embryonic (fetal) somatic cells, neonatal (fetal) somatic cells, and mature healthy or affected somatic cells. Somatic cells may be primary-cultured cells, subcultured cells, or established cells. Specific examples of somatic cells include: (1) tissue stem cells, such as neural stem cells, hematopoietic stem cells, mesenchymal stem cells, and dental pulp stem cells (i.e., somatic stem cells); (2) tissue progenitor cells; (3) differentiated cells, such as lymphocytes, epidermic cells, endothelial cells, muscle cells, fibroblasts (e.g., skin cells), hair cells, hepatic cells, gastric mucosal cells, intestinal cells, splenic cells, pancreatic cells (e.g., pancreatic exocrine cells), brain cells, pneumocytes, nephrocytes, and adipocytes.

When iPS cells are used as materials for transplantation, use of somatic cells having the same or substantially the same HLA genotype as that of a recipient is preferable, so that rejection would not occur. When HLA genotypes are "substantially the same," such HLA genotypes are concordant with each other to the extent that an immunosuppressive agent is able to suppress immune responses to the transplanted cells. For example, such somatic cells have HLA genotypes exhibiting concordance in 3 loci; i.e., HLA-A, HLA-B, and HLA-DR, or in 4 loci; i.e., HLA-A, HLA-B, HLA-DR, and HLA-C.

(E) Nuclear Transfer-Derived ES Cells from Cloned Embryos

"nt ES cells" are nuclear transfer-derived ES cells produced from cloned embryos, and such ES cells have substantially the same properties as fertilized egg-derived ES cells (T. Wakayama et al., 2001, Science, 292: 740-743; S. Wakayama et al., 2005, Biol. Reprod., 72: 932-936; J. Byrne et al., 2007, Nature, 450: 497-502). Specifically, nuclear transfer ES cells (i.e., nt ES cells) are ES cells that are established from embryoblasts of blastocysts derived from cloned embryos resulting from substitution of an unfertilized egg nucleus with a somatic cell nucleus. nt ES cells are produced by the technique of nuclear transfer (J. B. Cibelli et al., 1998, Nature Biotechnol., 16: 642-646) in combination with the technique of ES cell production (Kiyoka Wakayama et al., 2008, Experimental Medicine, Vol. 25, No. 5 (extra edition), pp. 47-52). In the case of nuclear transfer, somatic cell nuclei are injected into enucleated unfertilized eggs of mammalian animals, and culture is conducted for several hours. Thus, such cells can be reprogrammed.

(F) Multilineage-Differentiating Stress Enduring Cells (Muse Cells)

Muse cells are pluripotent stem cells produced by the method described in WO 2011/007900. More specifically, Muse cells are pluripotent cells that are obtained by treating fibroblasts or myeloid interstitial cells with trypsin for a long period of time (preferably for 8 hours or 16 hours) and conducting float culture. Such cells are positive for SSEA-3 and CD105.

[Kit for Inducing Pluripotent Stem Cells to Differentiate into Alveolar Epithelial Progenitor Cells]

The present invention provides a kit used for inducing pluripotent stem cells to differentiate into alveolar epithelial progenitor cells or producing alveolar epithelial progenitor cells from pluripotent stem cells. The kit may comprise growth factors, compounds, a medium, a cell detachment solution, and an agent for coating the culture vessel used for the induction of differentiation. The kit may further comprise documents and/or instructions describing the procedure for the induction of differentiation.

[Method for Selecting Alveolar Epithelial Progenitor Cells]

In the present invention, alveolar epithelial progenitor cells may constitute a population of cells including alveolar epithelial progenitor cells. In the present invention, a population of cells including alveolar epithelial progenitor cells preferably includes 50%, 60%, 70%, 80%, or 90% or more alveolar epithelial progenitor cells.

Accordingly, the present invention provides a method for extracting alveolar epithelial progenitor cells. The cells to be extracted may be alveolar epithelial progenitor cells obtained by the method described above or cells obtained in the process for producing the same, which takes place after the completion of Step (3) of culture in a medium containing BMP4, retinoic acid, and a GSK3β inhibitor or Step (4) of culture in a medium containing FGF10. Alveolar epithelial progenitor cells can be extracted with the use of a reagent having CPM-specific affinity. While CPM had been known as a marker of adult type I alveolar epithelial cells, it was not previously known that CPM was expressed in progenitor cells during development. That is, use of CPM as a surface marker in the same manner as with NKX2-1 as a marker of alveolar epithelial progenitor cells has been found for the first time through the present invention.

Examples of reagents having specific affinity that can be used in the present invention include antibodies, aptamers, peptides, and compounds that specifically recognize the substances of interest, with antibodies or fragments thereof being preferable.

In the present invention, antibodies may be polyclonal or monoclonal antibodies. Such antibodies can be prepared in accordance with techniques well known in the art (Current protocols in Molecular Biology, Ausubel et al. (editors), 1987, John Wiley and Sons (publisher), Section 11.12-11.13). When the antibodies of the present invention are polyclonal antibodies, specifically, proteins encoded by CPM expressed in *E. coli* or mammalian cells and purified, oligopeptides having partial amino acid sequences, or glycolipids may be purified in accordance with conventional techniques, nonhuman animals such as rabbits may be immunized therewith, and antibodies of interest can be obtained from sera of the immunized animals in accordance with a conventional technique. In the case of monoclonal antibodies, in contrast, antibodies of interest can be obtained from hybridoma cells prepared via fusion of spleen cells obtained from immunized nonhuman animals to myeloma cells (Current protocols in Molecular Biology, Ausubel et al. (editors), 1987, John Wiley and Sons (publisher), Section 11.4-11.11). Examples of antibody fragments include a part of an antibody (e.g., an Fab fragment) and a synthetic antibody fragment (e.g., a single-stranded Fv fragment, ScFv). Antibody fragments, such as Fab and F(ab)2 fragments, can be prepared by a genetic engineering technique well known in the art. For example, antibodies reacting with CPM can be obtained from Leica Microsystems.

In order to recognize or separate cells that express CPM, reagents having relevant affinity may be bound or conjugated to substances that enable detection, such as a fluorescent label, a radioactive label, a chemoluminescent label, an enzyme, biotin, or streptoavidin, or substances that enable isolation and extraction, such as Protein A, Protein G, beads, or magnetic beads.

Alternatively, reagents having relevant affinity may be indirectly labeled. Labeling may be carried out in accordance with various techniques known in the art. For example, pre-labeled antibodies (secondary antibodies) that specifically bind to the antibodies described above may be used.

Alveolar epithelial progenitor cells can be extracted by, for example, a method comprising conjugating particles to a reagent having relevant affinity in order to precipitate the cells, a method involving the use of magnetic beads to select the cells with the aid of magnetism (e.g., MACS), a method involving the use of a cell sorter with the aid of a fluorescent label, or a method involving the use of a support upon which antibodies or the like are immobilized (e.g., a cell enrichment column).

[Agents for Treatment of Pulmonary Alveolar Diseases]

The alveolar epithelial progenitor cells obtained in the present invention can be administered to patients afflicted with diseases that destroy the pulmonary alveolus in the form of pharmaceutical preparations. The alveolar epithelial progenitor cells are prepared into the form of a sheet, and the sheet may be applied to the alveolar epithelium of a patient. Alternatively, the alveolar epithelial progenitor cells may be suspended in physiological saline or the like, and the suspension may then be directly implanted in the pulmonary alveolus of the patient. Accordingly, the present invention provides an agent for treatment of pulmonary alveolar diseases comprising alveolar epithelial progenitor cells obtained from pluripotent stem cells in the manner described above.

In the present invention, the number of alveolar epithelial progenitor cells contained in the agent for treatment of pulmonary alveolar diseases is not particularly limited, provided that the transplanted grafts are able to survive. The number of the cells may be adequately adjusted in accordance with lesion size or body size.

EXAMPLES

Hereafter, the present invention is described in greater detail with reference to the examples, although the technical scope of the present invention is not limited to these examples.

[iPS Cell Culture]

Human iPS cells (201B7) were provided by Professor Yamanaka at Kyoto University and cultured in accordance with a conventional technique (Takahashi K, et al. Cell, 131: 861-872, 2007). In accordance with the method described in Mae S., et al, Nat. Commun., 4: 1367, 2013, according to a gene knock-in technique, SFTPC-reporter 201B7 was produced by introducing an EGFP sequence into a site downstream of the SFTPC initiation codon of the human iPS cells (201B7).

[Induction of Alveolar Epithelial Progenitor Cells]

FIG. 1 shows a scheme for producing alveolar epithelial progenitor cells from pluripotent stem cells such as iPS cells.

The alveolar epithelial progenitor cells were induced by detaching human iPS cells with the use of Accutase, seeding the cells in a 24-well plate coated with Matrigel at $2.0 \times 10^5$ cells/well or in a 6-well plate coated with Matrigel at $9.6 \times 10^5$ cells/well, and conducting culture under the conditions described below (FIGS. 1A and 1B).

(Step 1)

The seeded cells (Day 0) were cultured in basal medium 1 (RPMI1640 (Nacalai Tesque) containing 2% B27 (Life Technologies) and a 0.5% penicillin/streptomycin stock solution (Life Technologies)) supplemented with 100 ng/ml Activin A (R&D Systems), 1 µM CHIR99021 and 10 µM Y-27632. On the following day (Day 1), the medium was exchanged with basal medium 1 containing 100 ng/ml Activin A, 1 µM CHIR99021, and 0.25 mM NaB, the medium was exchanged with another medium under the same conditions on the following day (Day 2) and 3 days later (Day 4), and culture was conducted for 5 days.

Alternatively, the seeded cells (Day 0) were cultured in basal medium 1 supplemented with 100 ng/ml Activin A, 1 µM CHIR99021, and 10 µM Y-27632. On the following day (Day 1), the medium was exchanged with basal medium 1 containing 100 ng/ml Activin A, 1 µM CHIR99021, 10 µM Y-27632, and 0.125 mM or 0.25 mM NaB, the medium was exchanged with basal medium 1 containing 100 ng/ml Activin A, 1 µM CHIR99021, and 0.125 mM or 0.25 mM NaB on the following day (Day 2), and the medium was exchanged with another medium under the same conditions 3 days later (Day 4).

(Step 2)

The cells obtained in Step 1 (Day 6) were cultured in basal medium 2 (DMEM/F12 medium (Life Technologies) containing 1% Glutamax supplement (Life Technologies), 2% B27 supplement, 1% N2 supplement (Life Technologies), 0.8% StemSure™ 50 mmol/l monothioglycerol solution (Wako), 50 µg/ml L-ascorbic acid (Sigma Aldrich), and 0.5% penicillin/streptomycin stock solution) supplemented with 200 ng/ml or 100 ng/ml hNoggin (R&D Systems) and 10 µM SB-431542 for 4 days. In this case, the medium was exchanged with another medium under the same conditions every other day.

(Step 3)

The cells obtained in Step 2 (Day 10) were cultured in basal medium 2 containing 100 ng/ml hBMP4 (HumanZyme, Inc.), 0.05 µM all-trans retinoic acid (ATRA), and 2.5 µM CHIR99021 for 4 days. In this case, the medium was exchanged with another medium under the same conditions every other day.

(Step 4)

The cells obtained in Step 3 (Day 14) were cultured in basal medium 2 containing 100 ng/ml FGF10 (Wako) for 7 days. In this case, the medium was exchanged with another medium under the same conditions every other day.

(Step 5)

After the media were exchanged, the cells obtained in Step 4 (Day 21) were cultured in basal medium 3 (Ham's F12 media (Wako) containing 3.33% BSA Fraction V Solution (7.5%) (Life Technologies), 15 mM HEPES (Sigma Aldrich), 0.8 mM $CaCl_2$ (Nacalai Tesque), 1% ITS Premix (BD), and 0.5% penicillin/streptomycin stock solution) containing 50 nM dexamethasone (Sigma Aldrich), 0.1 mM 8-Br-cAMP (Biolog Life Science Institute), 0.1 mM 3-isobutyl-1-methylxanthine (IBMX) (Wako), and 100 ng/ml or 50 ng/ml KGF (Wako). Thereafter, the medium was exchanged with another medium under the same conditions every other day. The alveolar epithelial progenitor cells obtained were analyzed 4 days later (Day 25).

[Cell Analysis]

(1) After the Completion of Step 3

Figure 5:
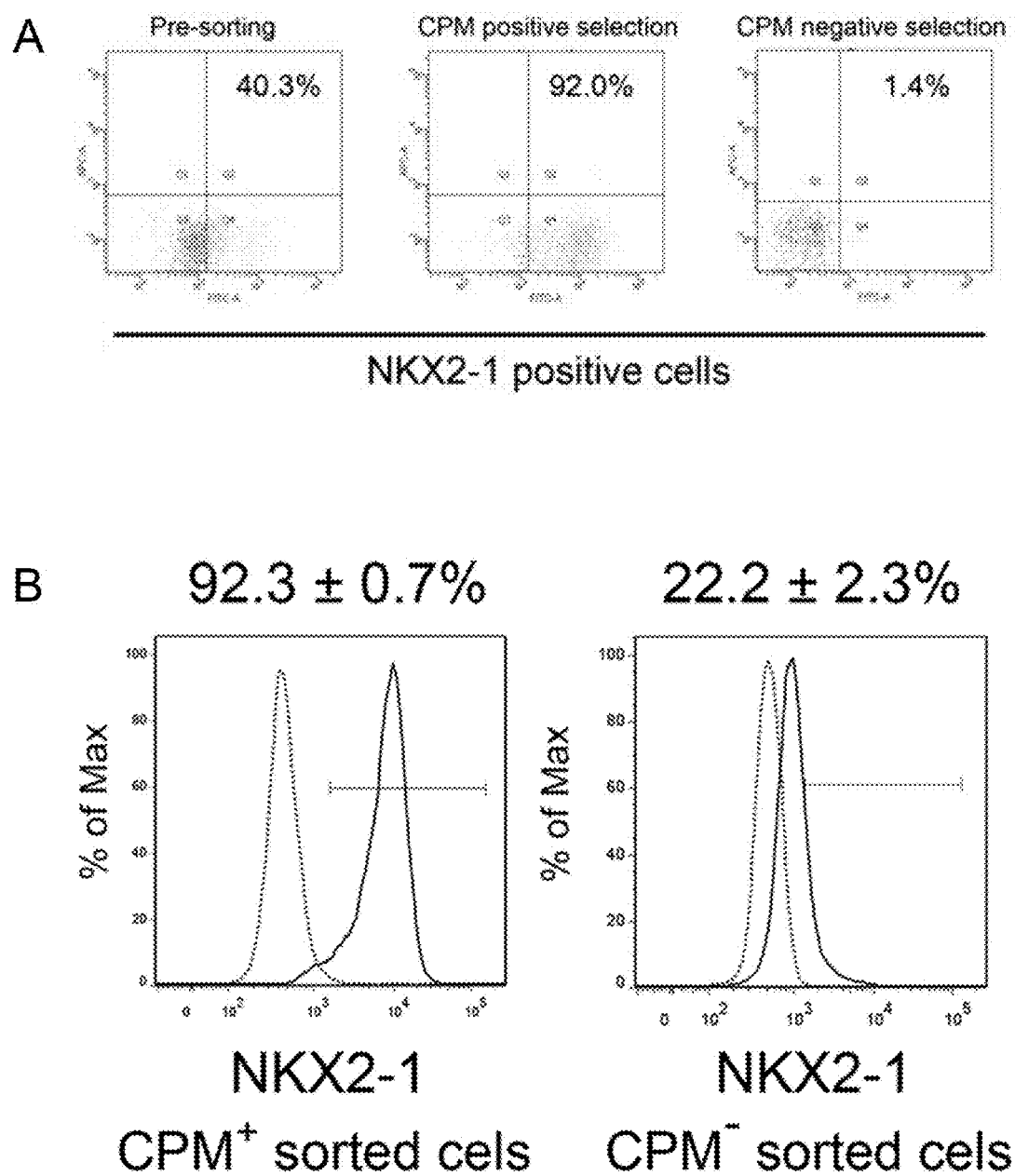
FIG. 5A shows percentages of NKX2-1-positive cells among the MACS-sorted cells after the completion of Step 3. In the figure, "Pre-sorting" shows the results for the cells before sorting via MACS, "CPM positive selection" shows the results for the MACS-sorted CPM-positive cells, and "CPM negative selection" shows the results for the MACS-sorted CPM-negative cells.
FIG. 5B shows percentages of NKX2-1-positive cells among the MACS-sorted cells after the completion of Step 3. In the figure, "CPM$^+$ sorted cells" shows percentages of NKX2-1-positive cells among the MACS-sorted CPM-positive cells (92.3±0.7%), and "CPM$^−$ sorted cells" shows percentages of NKX2-1-positive cells among the MACS-sorted CPM-negative cells (22.2±2.3%).
Figure 6:
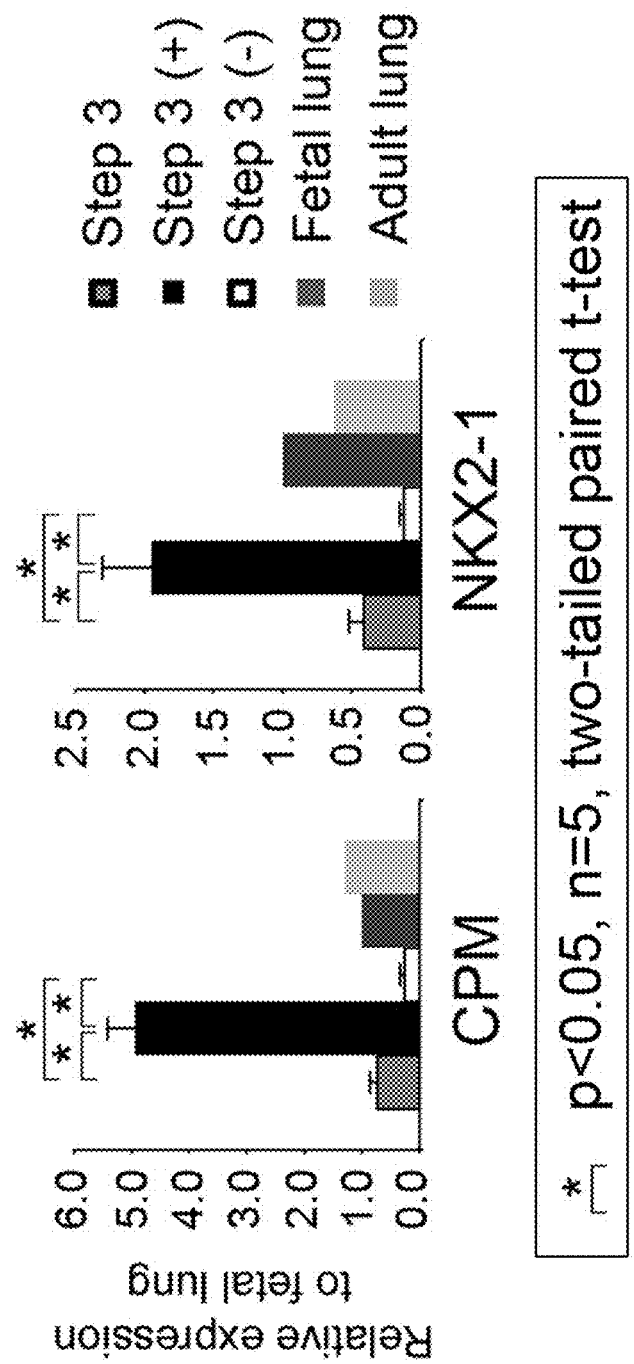
FIG. 6 shows the assay results of CPM mRNA levels (left) and NKX2-1 mRNA levels (right) in the MACS-sorted cells on the basis of CPM markers via quantitative PCR after the completion of Step 3. "Step 3" shows the results for the cells before sorting, "Step 3 (+)" shows the results for the CPM-positive cells, "Step 3 (−)" shows the results for the CPM-negative cells, "Fetal Lung" shows the results for the fetal pneumocytes, and "Adult Lung" shows the results for the adult pneumocytes.

After the completion of Step 3 (Day 14), the cells were subjected to immunostaining so as to inspect CPM and NKX2-1 expression. As a result, cells positive for both such markers were identified (FIGS. 2A and 2B). In addition, CPM-positive cells were separated from the cells obtained on Day 14 using MACS (Miltenyi Biotec) (FIGS. 3A and 3B), and the obtained cells were allowed to adhere to glass slides via cytospinning, followed by immunostaining. As a result, many thereof were found to also be positive for NKX2-1 (FIGS. 4A and 4B). The cells were analyzed using a flow cytometer. As a result, 92% of the CPM-positive cells obtained by MACS were found to be NKX2-1-positive (FIGS. 5A and 5B). Also, CPM-positive cells identified via MACS were subjected to quantitative RT-PCR, so as to assay CPM and NKX2-1 mRNA levels. As a result, sorting of CPM-positive cells was found to result in a remarkable increase in CPM and NKX2-1 mRNA levels (FIG. 6).

(2) After the Completion of Step 4

Figure 7:
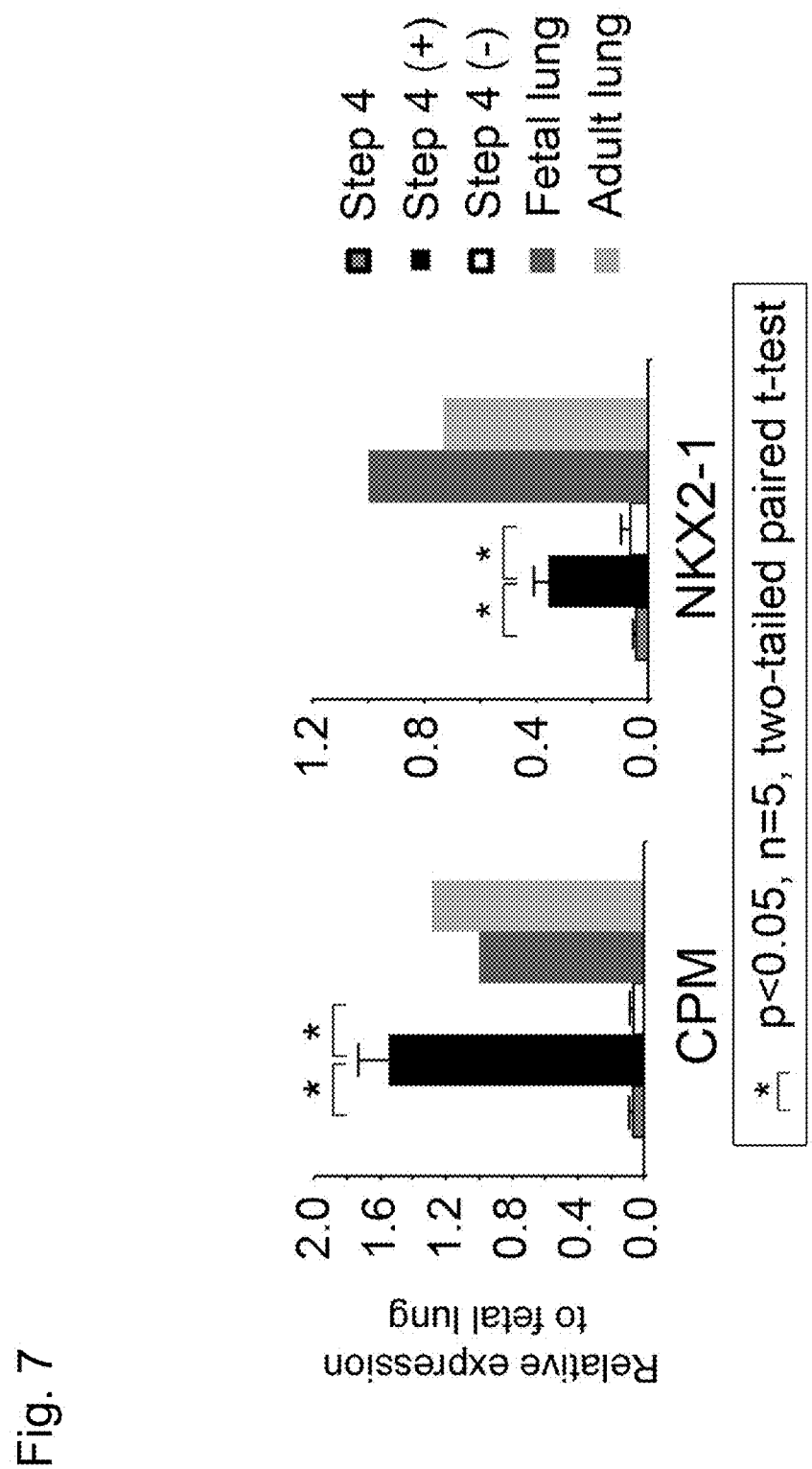
FIG. 7 shows the assay results of CPM mRNA levels (left) and NKX2-1 mRNA levels (right) in the MACS-sorted cells via quantitative PCR after the completion of Step 4. "Step 4" shows the results for the cells before sorting, "Step 4 (+)" shows the results for the CPM-positive cells, "Step 4 (−)" shows the results for the CPM-negative cells, "Fetal Lung" shows the results for the fetal pneumocytes, and "Adult Lung" shows the results for the adult pneumocytes.

After the completion of Step 4 (Day 21), CPM-positive cells were separated from cells using MACS, and the CPM and NKX2-1 mRNA levels were assayed via quantitative RT-PCR. As a result, sorting of CPM-positive cells was found to result in a remarkable increase in CPM and NKX2-1 mRNA levels (FIG. 7).

(3) After the Completion of Step 5

Figure 8:
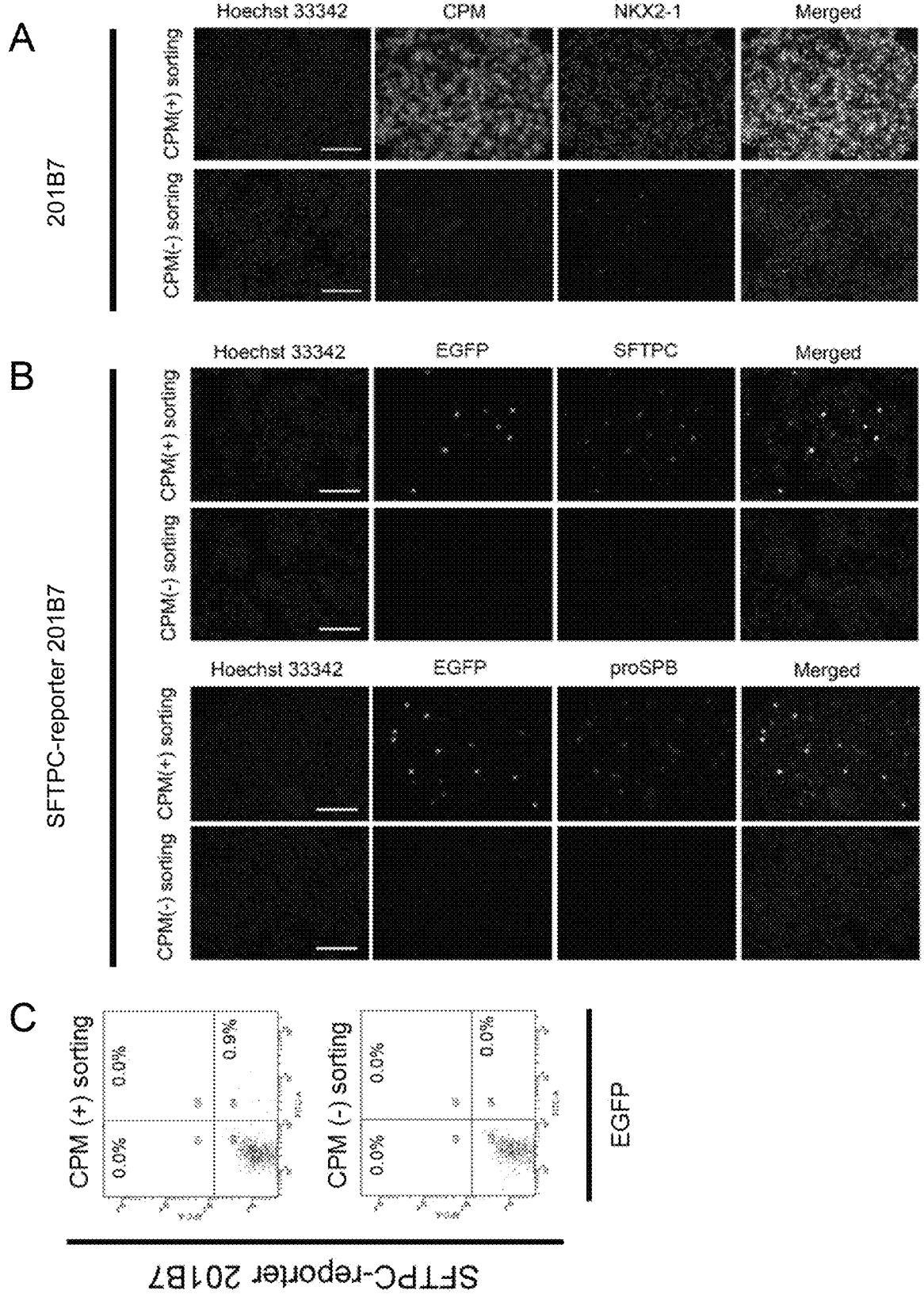
FIG. 8A shows images of immunostained iPS cells (201B7) in the MACS-sorted CPM-positive cells after the completion of Step 5.
FIG. 8B shows images of immunostained iPS cells (SFTPC reporter cells; SFTPC-reporter 201B7) in the MACS-sorted CPM-positive cells after the completion of Step 5.
FIG. 8C shows percentages of EGFP-positive iPS cells (SFTPC reporter cells; SFTPC-reporter 201B7) among the MACS-sorted CPM-positive cells after the completion of Step 5.

After the completion of Step 5 (Day 25), CPM-positive cells were separated from cells using MACS, and the obtained cells were allowed to adhere to glass slides via cytospinning, followed by immunostaining. As a result, many thereof were found to also be positive for NKX2-1 (FIG. 8A). In addition, the cells induced to differentiate in the same manner with the use of SFTPC-reporter 201B7 were subjected to immunostaining. As a result, the presence of SFTPC- or proSPB-positive cells was observed in the CPM-positive cells (FIG. 8B). The percentage of the SFTPC-positive cells was found to be about 0.9% as a result of flow cytometric analysis (FIG. 8C).

Figure 9:
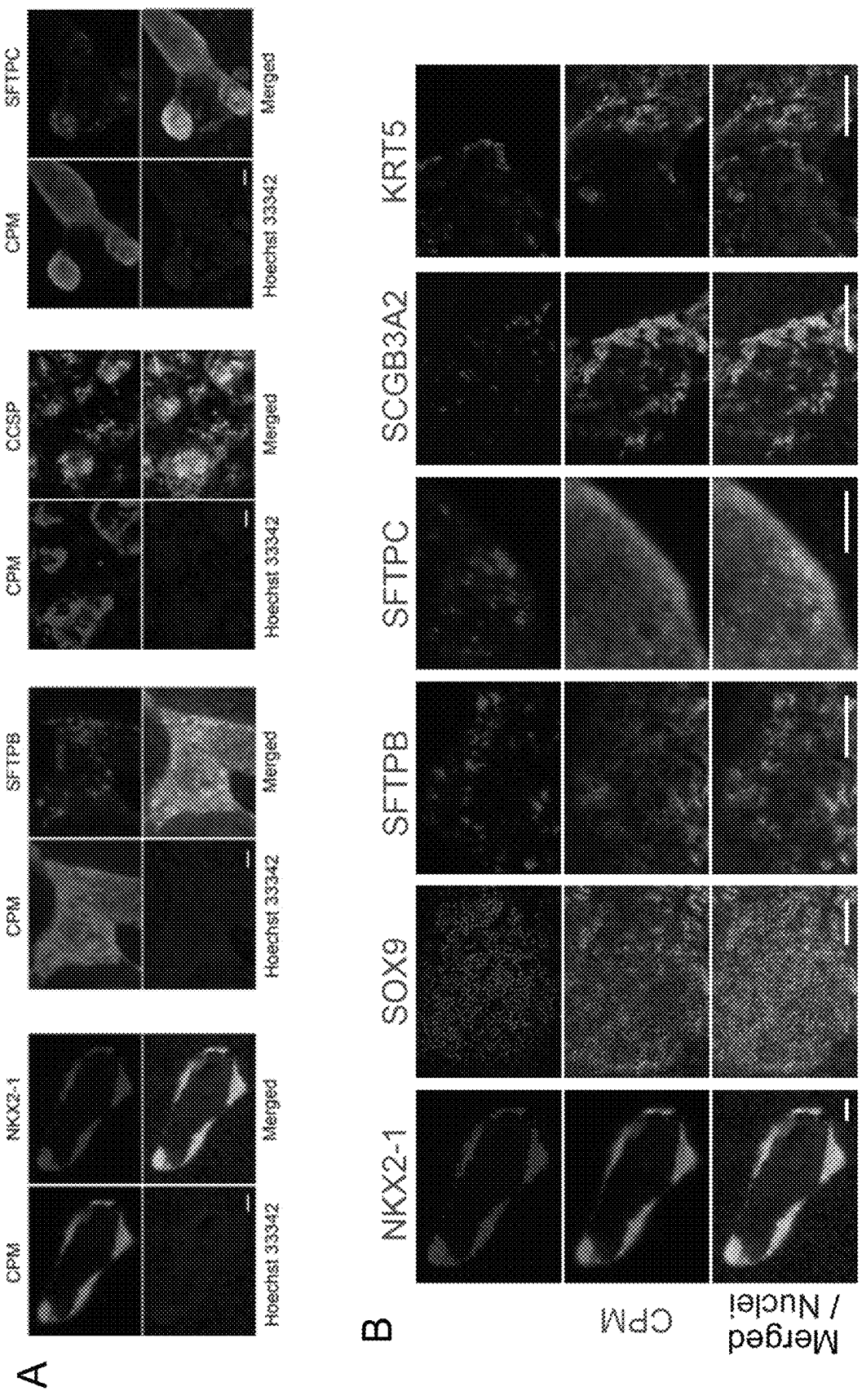
FIG. 9A and FIG. 9B each show an image of immunostained cells after the completion of Step 5.
Figure 10:
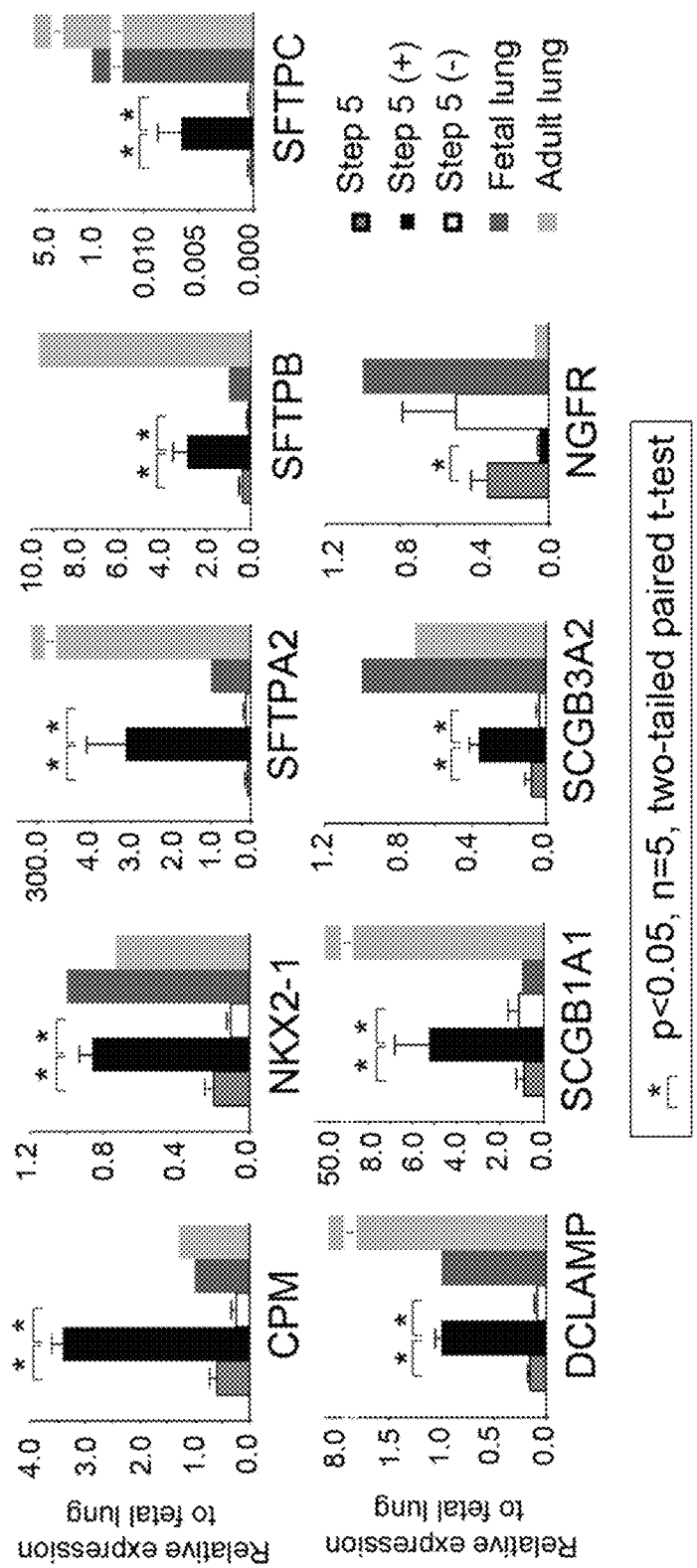
FIG. 10 shows the assay results of mRNA levels via quantitative PCR of CPM, NKX2-1, SFTPA2, SFTPB, SFTPC, DCLAMP, CCSP (SCGB1A1), SCGB3A2, and NGFR in the MACS-sorted cells after the completion of Step 5. "Step 5" shows the results for the cells before sorting, "Step 5 (+)" shows the results for the CPM-positive cells, "Step 5 (−)" shows the results for the CPM-negative cells, "Fetal Lung" shows the results for the fetal pneumocytes, and "Adult Lung" shows the results for the adult pneumocytes.

Subsequently, the cells (201B7) after the completion of Step 5 (Day 25) were subjected to immunostaining, and CPM-, NKX2-1-, SFTPB-, SFTPC-, and CCSP-positive cells were identified (FIGS. 9A and 9B). In this case, marker genes were found to be also positive for CPM. In addition, CPM-positive cells obtained using MACS were subjected to quantitative RT-PCR, so as to assay the CPM, NKX2-1, SFTPA2, SFTPB, DCLAMP, SFTPC, CCSP, and NGFR mRNA levels. As a result, sorting of CPM-positive cells was found to result in a remarkable increase in the CPM and NKX2-1 mRNA levels (FIG. 10).

As described above, it was demonstrated that alveolar epithelial cells or progenitor cells thereof could be induced from iPS cells by the method of the present invention.

[Effects of CPM Marker]

Figure 11:
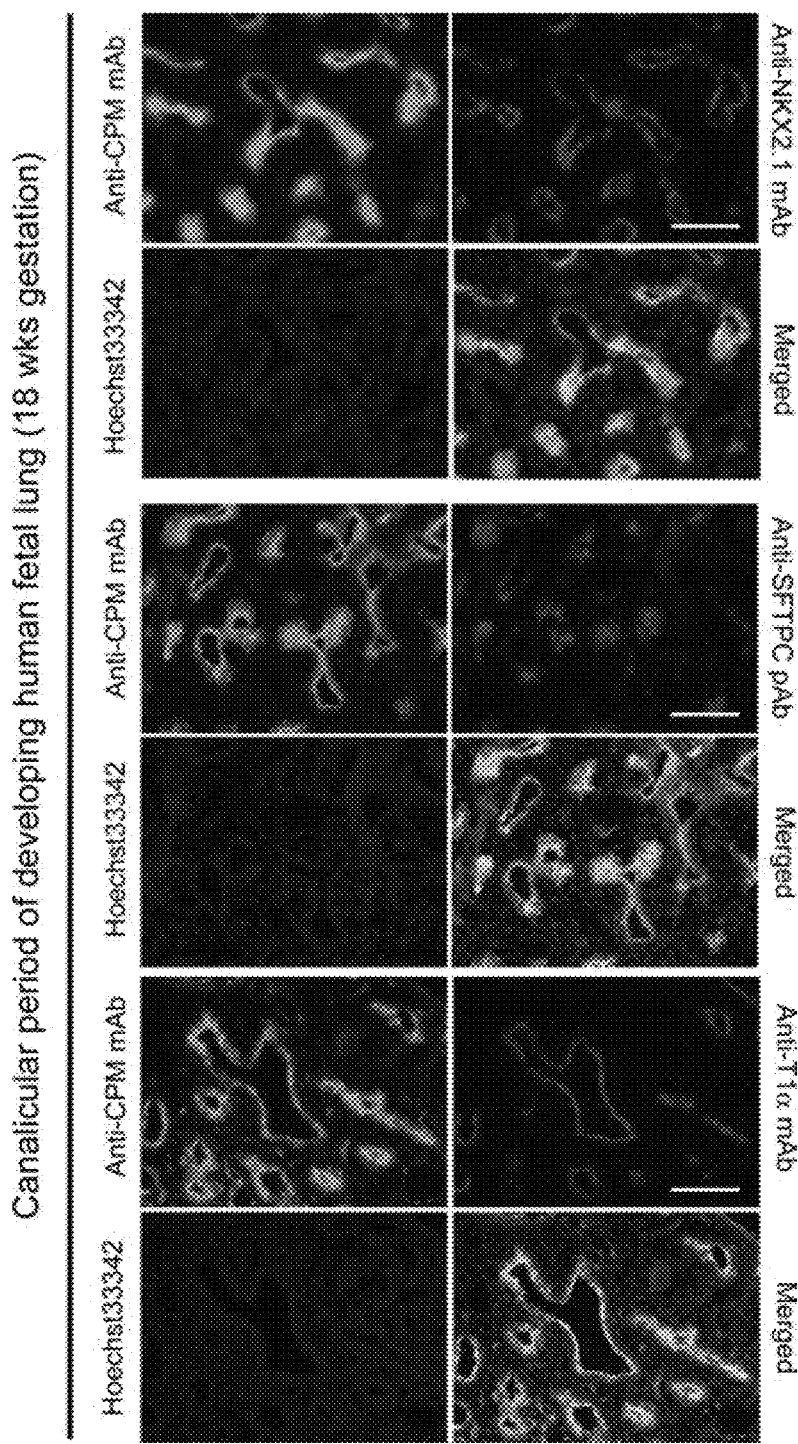
FIG. 11 shows images of CPM in the human fetal lung tissue subjected to staining together with NKX2-1, SFTPC, or T1α serving as a marker of the prenatal period, the adenoid period, or the canalicular period of the lung, respectively.
Figure 12:
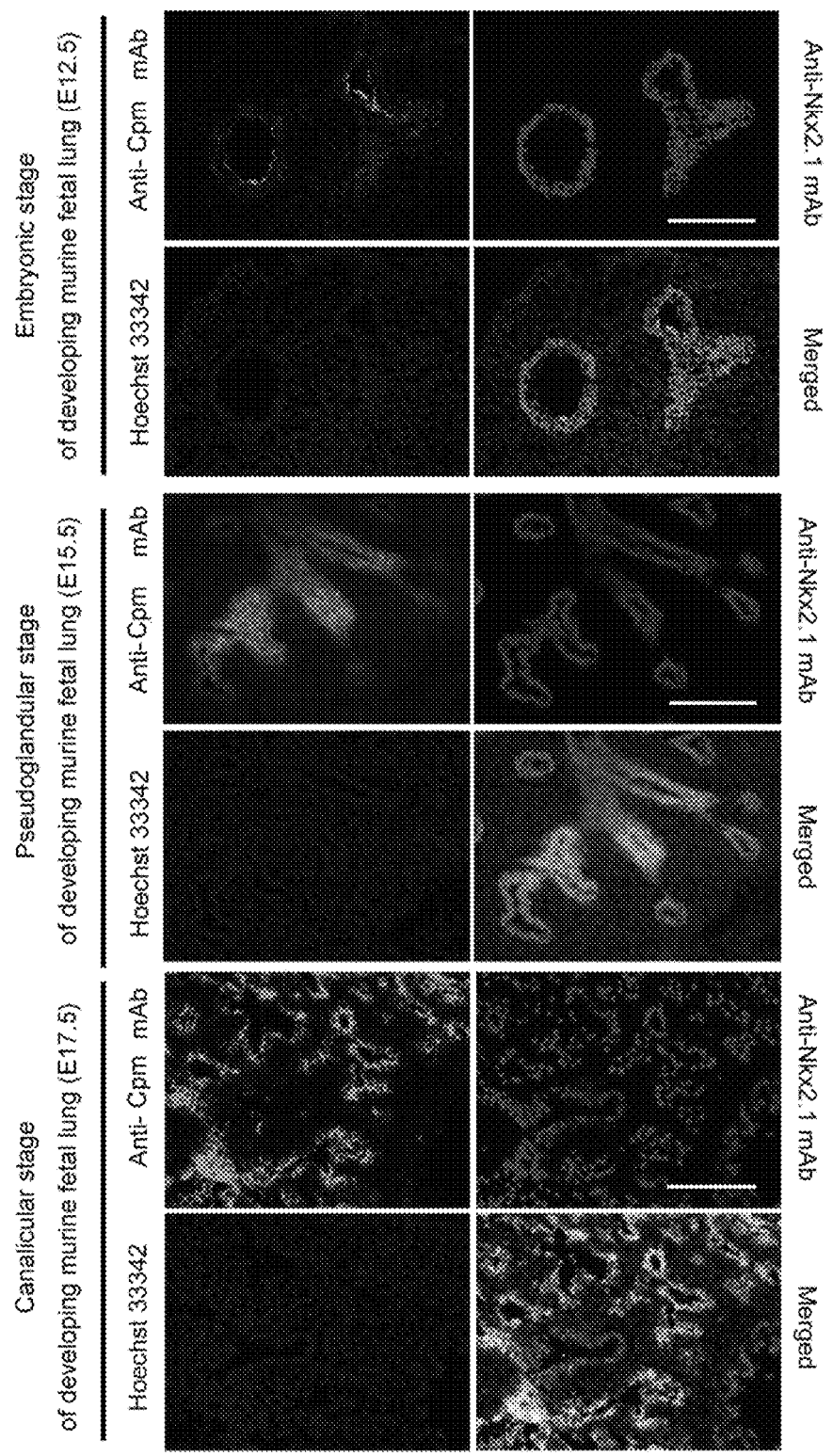
FIG. 12 shows images of CPM in the mouse lung tissue at relevant prenatal periods (E12.5, E15.5, and E17.5) subjected to staining together with NKX2-1 serving as a marker of the prenatal period, the adenoid period, or the canalicular period of the lung, respectively.

CPM expression in human fetus-derived lung tissue (FIG. 11) and mouse fetus-derived lung tissue (E12.5, E15.5, and E17.5) (FIG. 12) was inspected. As a result, expression of CPM in combination with NKX2-1, SFTPC, and T1α was observed. Accordingly, CPM was found to be capable of recognizing alveolar epithelial progenitor cells at an early stage, such as during the prenatal period (humans: 3 to 7 weeks in the prenatal period; mice: 9 to 14 days in the prenatal period), in addition to the canalicular period of lung development (humans: 16 to 24 weeks in the prenatal period; mice: 16.5 to 17.5 days in the prenatal period) and the adenoid period (humans: 7 to 16 weeks in the prenatal period; mice: 14.0 to 16.5 days in the prenatal period).

As described above, it was found that alveolar epithelial progenitor cells could be recognized and extracted with the use of CPM as an indicator.

[Three-Dimensional Culture]

Figure 13:
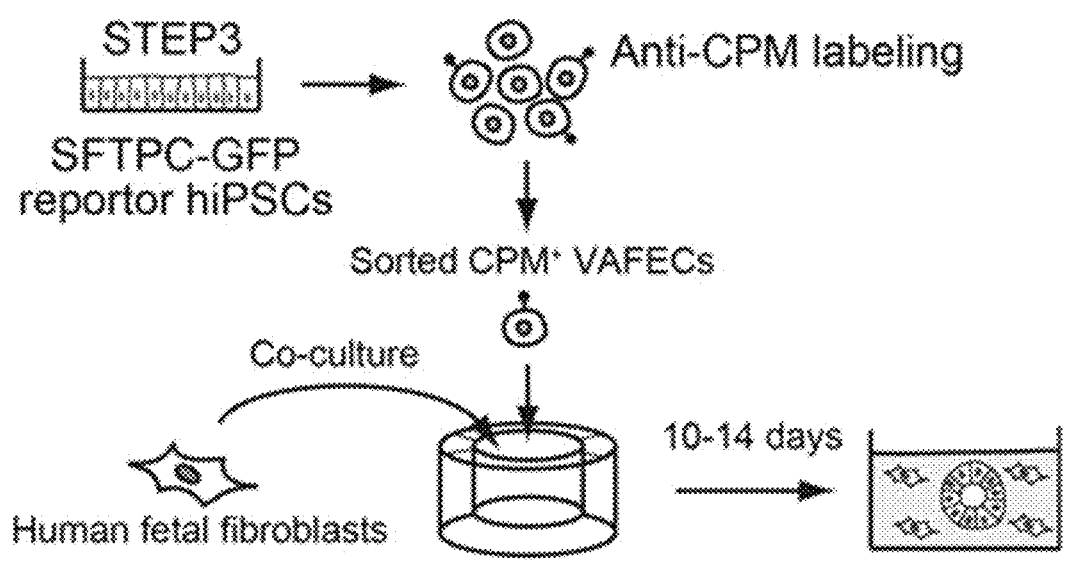
FIG. 13 shows a summary of a method of sorting CPM-positive cells from among the cells after the completion of Step 3 and culturing the sorted cells together with human fetal pulmonary fibroblasts.

As described above, the CPM-positive cells ($2 \times 10^4$ cells) extracted via MACS obtained after the completion of Step 3 with the use of SFTPC-reporter 201B7 were transferred to 12-well Cell Culture Inserts (BD Biosciences) supplemented with 400 μl of medium containing Matrigel in combination with basal medium 3 containing 50 nM dexamethasone, 0.1 mM 8-Br-cAMP, 0.1 mM IBMX, and 10 ng/ml KGF at a ratio of 1:1 together with $2 \times 10^6$ human fetus-derived pulmonary fibroblasts (PP002-F-1349, DV Biologics). Also, basal medium 3 containing 10 μM Y-27632, 50 nM dexamethasone, 0.1 mM 8-Br-cAMP, 0.1 mM IBMX, and 10 ng/ml KGF was added to the lower layer of the Cell Culture Inserts so as to form spheroids (cell masses), and culture was conducted for 10 to 12 days (FIG. 13). The resulting spheroids were inspected using a transmission electron microscope and found to be cells having lamella-like structures (FIG. 14A).

In addition, the spheroids were subjected to hematoxylin-eosin staining, and CPM(+)-cell-derived spheroids were found to be in the form of cystic pseudo-lamellar, cylindrical, or cubic cells having cytoplasm that would be stained dark pink, unlike CPM(−)-cell-derived spheroids having cytoplasm of pale color (FIG. 15A). These cells were double positive for both NKX2-1 and CPM. In addition, these cells included SFTPC-positive cells (FIG. 15B). In this case, AQP5-positive cells as markers of type I alveolar epithelial cells were found to be present adjacent to SFTPC-positive cells.

Figure 16:
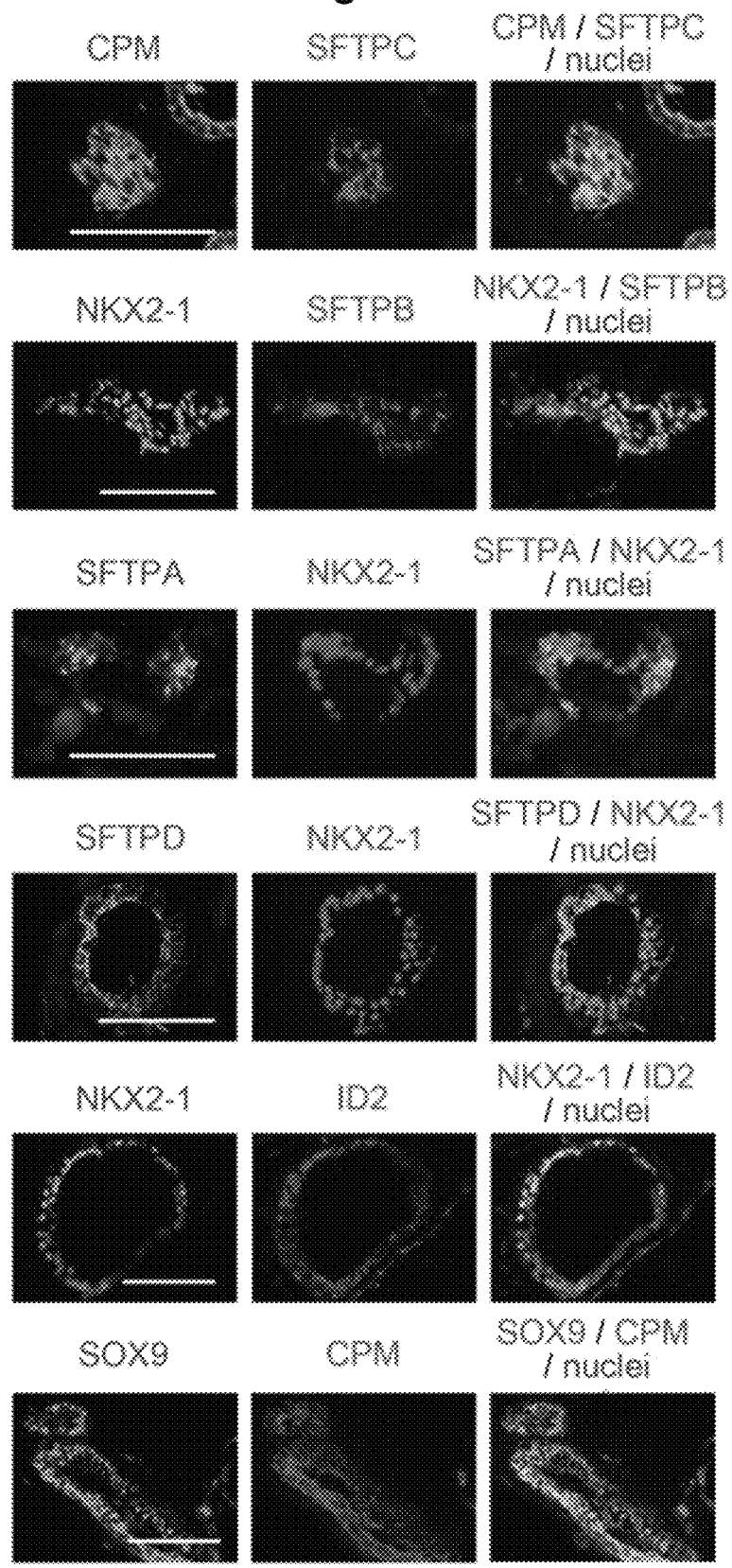
FIG. 16 shows images of the spheroids immunostained with the CPM, NKX2-1, SFTPC, SFTPB, SFTPA, SFTPD, ID2, and SOX9 antibodies following the three-dimensional culture of the CPM-positive cells after the completion of Step 3. The images on the right show images of alveolar epithelial cell-associated proteins subjected to dual staining with either CPM or NKX2-1.

The alveolar epithelial cell marker expression was inspected and SFTPA, SFTPB, SFTPC, and SFTPD were found to be expressed in the CPM- and NKX2-1-positive cells (FIG. 16). As a result of quantitative PCR, the expression levels of these genes were found to have been elevated via three-dimensional culture. In addition, expression of SOX9 and ID2, which are indicators for induction of the peripheral airway, was observed in CPM- and NKX2-1-positive cells in several spheroids (FIG. 16).

Figure 17:
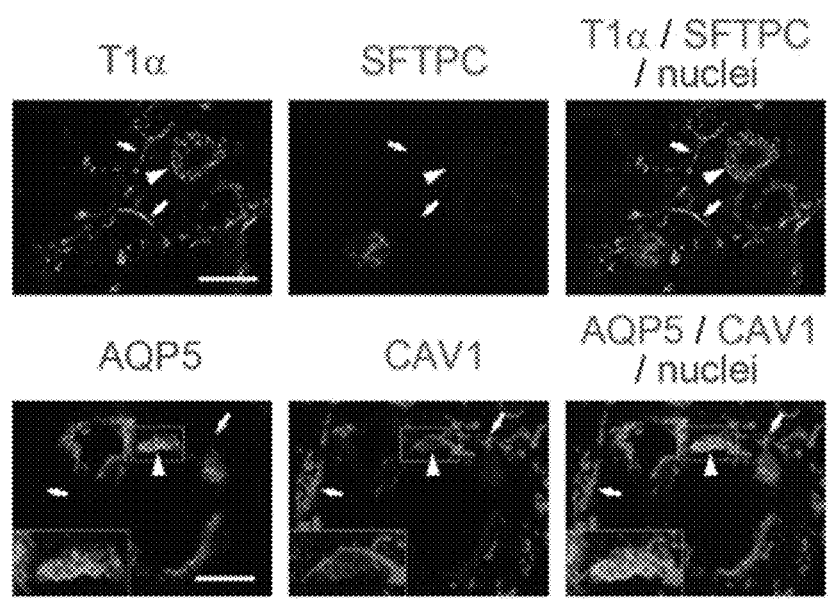
FIG. 17 shows images of the spheroids immunostained with the T1α, SFTPC, AQP5, and CAV1 antibodies following the three-dimensional culture of the CPM-positive cells after the completion of Step 3.

While PDPN and CAV1 were expressed in fibroblast-like cells in the vicinity of the spheroids (indicated with arrows), they were also expressed in the spheroids (indicated with arrowheads) (FIG. 17).

As described above, it was found that alveolar epithelial cells were induced from CPM-positive cells, and CPM was found to be a useful marker of progenitor cells of alveolar epithelial cells. In addition, the CPM-positive cells obtained were found to be induced into mature alveolar epithelial cells via three-dimensional co-culture thereof with human fetus-derived pulmonary fibroblasts.

INDUSTRIAL APPLICABILITY

The method of the present invention enables production of alveolar epithelial progenitor cells from pluripotent stem cells.

All publications, patents, and patent applications cited herein are incorporated herein by reference in their entirety.

The invention claimed is:

1. A method for producing alveolar epithelial progenitor cells from pluripotent stem cells comprising Steps (1) to (6):
   (1) culturing pluripotent stem cells in a medium containing activin A and a glycogen synthase kinase 3β (GSK3β) inhibitor;
   (2) culturing the cells obtained in Step (1) in a medium containing a bone morphogenic protein (BMP) inhibitor and a transforming growth factor β (TGFβ) inhibitor;
   (3) culturing the cells obtained in Step (2) in a medium containing BMP4, retinoic acid, and a GSK3β inhibitor;
   (4) culturing the cells obtained from Step (3) in a medium containing fibroblast growth factor 10 (FGF10);
   (5) culturing the cells obtained from Step (4) in a medium containing a steroid drug, a cyclic adenosine monophosphate (cAMP) derivative, a phosphodiesterase inhibitor, and a keratinocyte growth factor (KGF); and
   (6) extracting carboxypeptidase M (CPM)-positive cells as alveolar epithelial progenitor cells using the CPM as a marker following Step (5).

2. The method according to claim 1, wherein the medium of Step (1) further comprises a Rho kinase (ROCK) inhibitor and/or a histone deacetylase (HDAC) inhibitor.

3. The method according to claim 1, wherein Step (1) comprises culturing for 6 days or longer, Step (2) comprises culturing for 4 days or longer, and Step (3) comprises culturing for 4 days or longer.

4. The method according to claim 1, wherein the GSK3β inhibitor is CHIR99021, the BMP inhibitor is Noggin, and the TGFβ inhibitor is SB431542.

5. The method according to claim 2, wherein the ROCK inhibitor is Y-27632 and/or the HDAC inhibitor is sodium butyrate.

6. The method according to claim 1, wherein Step (4) comprises culturing for 7 days or longer.

7. The method according to claim 1, wherein Step (5) comprises culturing for 4 days or longer.

8. The method according to claim 1, wherein the steroid drug is dexamethasone, the cAMP derivative is 8Br-cAMP, and the phosphodiesterase inhibitor is 3-isobutyl-1-methyl-xanthine (IBMX).

9. The method according to claim 1, wherein the alveolar epithelial progenitor cells are human alveolar epithelial progenitor cells.

10. A method for producing alveolar epithelial progenitor cells from pluripotent stem cells comprising Steps (1) to (3b):
    (1) culturing pluripotent stem cells in a medium containing activin A and a glycogen synthase kinase 3β (GSK3β) inhibitor;
    (2) culturing the cells obtained in Step (1) in a medium containing a bone morphogenic protein (BMP) inhibitor and a transforming growth factor β (TGFβ) inhibitor;
    (3a) culturing the cells obtained in Step (2) in a medium containing BMP4, retinoic acid, and a GSK3β inhibitor; and
    (3b) extracting carboxypeptidase M (CPM)-positive cells as alveolar epithelial progenitor cells using the CPM as a marker following Step (3a).

11. The method according to claim 10, wherein the medium of Step (1) further comprises a Rho kinase (ROCK) inhibitor and/or a histone deacetylase (HDAC) inhibitor.

12. The method according to claim 10, wherein Step (1) comprises culturing for 6 days or longer, Step (2) comprises culturing for 4 days or longer, and Step (3a) comprises culturing for 4 days or longer.

13. The method according to claim 10, wherein the GSK3β inhibitor is CHIR99021, the BMP inhibitor is Noggin, and the TGFβ inhibitor is SB431542.

14. The method according to claim 10, wherein the alveolar epithelial progenitor cells are human alveolar epithelial progenitor cells.

15. A method for producing alveolar epithelial cells from pluripotent stem cells comprising Steps (1) to (3c):
    (1) culturing pluripotent stem cells in a medium containing activin A and a glycogen synthase kinase 3β (GSK3β) inhibitor;
    (2) culturing the cells obtained in Step (1) in a medium containing a bone morphogenic protein (BMP) inhibitor and a transforming growth factor β (TGFβ) inhibitor;
    (3a) culturing the cells obtained in Step (2) in a medium containing BMP4, retinoic acid, and a GSK3β inhibitor;
    (3b) extracting carboxypeptidase M (CPM)-positive cells as alveolar epithelial progenitor cells using the CPM as a marker following Step (3a); and
    (3c) co-culturing the extracted alveolar epithelial progenitor cells together with human fetal pulmonary fibroblasts, following Step (3b).

16. The method according to claim 15, wherein the medium of Step (1) further comprises a Rho kinase (ROCK) inhibitor and/or a histone deacetylase (HDAC) inhibitor.

17. The method according to claim 15, wherein Step (1) comprises culturing for 6 days or longer, Step (2) comprises culturing for 4 days or longer, and Step (3a) comprises culturing for 4 days or longer.

18. The method according to claim 15, wherein the GSK3β inhibitor is CHIR99021, the BMP inhibitor is Noggin, and the TGFβ inhibitor is SB431542.

19. The method according to claim 15, wherein the alveolar epithelial cells are human alveolar epithelial cells.

20. The method according to claim 15, wherein step (3c) is conducted by co-culturing in three-dimensional cell culture.

* * * * *